(12) United States Patent
Lavi et al.

(10) Patent No.: US 12,039,685 B2
(45) Date of Patent: Jul. 16, 2024

(54) METHODS, APPARATUS, AND SYSTEM FOR SYNCHRONIZATION BETWEEN A THREE-DIMENSIONAL VASCULAR MODEL AND AN IMAGING DEVICE

(71) Applicant: CathWorks Ltd., Kfar Saba (IL)

(72) Inventors: Ifat Lavi, Moshav Mishmeret (IL); Guy Lavi, Moshav Mishmeret (IL)

(73) Assignee: CathWorks Ltd., Kfar Saba (IL)

( * ) Notice: Subject to any disclaimer, the term of this patent is extended or adjusted under 35 U.S.C. 154(b) by 77 days.

(21) Appl. No.: 17/762,681

(22) PCT Filed: Sep. 23, 2020

(86) PCT No.: PCT/IB2020/058901
§ 371 (c)(1),
(2) Date: Mar. 22, 2022

(87) PCT Pub. No.: WO2021/059165
PCT Pub. Date: Apr. 1, 2021

(65) Prior Publication Data
US 2022/0254131 A1  Aug. 11, 2022

Related U.S. Application Data

(60) Provisional application No. 62/904,147, filed on Sep. 23, 2019.

(51) Int. Cl.
*G06T 19/20* (2011.01)
*A61B 6/00* (2024.01)
(Continued)

(52) U.S. Cl.
CPC ............ *G06T 19/20* (2013.01); *A61B 6/4441* (2013.01); *A61B 6/463* (2013.01); *A61B 6/467* (2013.01);
(Continued)

(58) Field of Classification Search
None
See application file for complete search history.

(56) References Cited

U.S. PATENT DOCUMENTS

| | | |
|---|---|---|
| 5,150,292 A | 9/1992 | Hoffmann et al. |
| 5,638,823 A | 6/1997 | Akay et al. |

(Continued)

FOREIGN PATENT DOCUMENTS

| | | |
|---|---|---|
| AU | 2010298333 | 1/2012 |
| CN | 104282009 | 1/2015 |

(Continued)

OTHER PUBLICATIONS

Chen et al.; "3-D Reconstruction of Coronary Arterial Tree to Optimize Angiographic Visualization;" IEEE Transactions on Medical Imaging, vol. 19, No. 4, Apr. 2000; pp. 318-336 (Year: 2000).*

(Continued)

*Primary Examiner* — Edward Martello
(74) *Attorney, Agent, or Firm* — Knobbe, Martens, Olson & Bear, LLP

(57) ABSTRACT

An apparatus for synchronizing a three-dimensional model of a patient's coronary arteries with an orientation of a medical imaging device is disclosed. In an example, an apparatus is configured to receive an indication that a three-dimensional model has been rotated. The indication includes a number of degrees of rotation of the three-dimensional model along a roll and/or pitch axis. The processor uses a correlation or transfer function to determine a rotational angulation position of the medical imaging device based on the number of degrees of rotation of the three-dimensional model along the roll and/or pitch axis. The processor transmits a command or instruction to the medical imaging device that is indicative of the desired (Continued)

rotational angulation position, thereby causing the medical imaging device to rotate to the desired position.

21 Claims, 14 Drawing Sheets

(51) Int. Cl.
  *A61B 6/46* (2024.01)
  *A61B 34/10* (2016.01)
  *G06T 7/32* (2017.01)
  *G06T 7/62* (2017.01)
  *G06T 7/70* (2017.01)

(52) U.S. Cl.
  CPC ............... *A61B 34/10* (2016.02); *G06T 7/32* (2017.01); *G06T 7/62* (2017.01); *G06T 7/70* (2017.01); *A61B 2034/105* (2016.02); *G06T 2207/10116* (2013.01); *G06T 2207/30101* (2013.01); *G06T 2210/41* (2013.01); *G06T 2219/2004* (2013.01); *G06T 2219/2016* (2013.01)

(56) References Cited

U.S. PATENT DOCUMENTS

| | | | |
|---|---|---|---|
| 6,047,080 A | 4/2000 | Chen et al. |
| 6,236,878 B1 | 5/2001 | Taylor et al. |
| 6,842,638 B1 | 1/2005 | Suri et al. |
| 7,113,623 B2 | 9/2006 | Chen et al. |
| 7,339,585 B2 | 3/2008 | Verstraelen et al. |
| 7,369,691 B2 | 5/2008 | Kondo et al. |
| 7,574,026 B2 | 8/2009 | Rasche et al. |
| 7,657,299 B2 | 2/2010 | Huizenga et al. |
| 7,693,315 B2 | 4/2010 | Krishnan et al. |
| 7,738,626 B2 | 6/2010 | Weese et al. |
| 7,808,503 B2 | 10/2010 | Duluk, Jr. et al. |
| 7,864,997 B2 | 1/2011 | Aben |
| 7,912,260 B2 | 3/2011 | Breeuwer et al. |
| 7,970,187 B2 | 6/2011 | Puts et al. |
| 8,073,224 B2 | 12/2011 | Strobel et al. |
| 8,086,000 B2 | 12/2011 | Weijers et al. |
| 8,090,164 B2 | 1/2012 | Bullitt et al. |
| 8,155,411 B2 | 4/2012 | Hof et al. |
| 8,298,147 B2 | 10/2012 | Huennekens et al. |
| 8,311,748 B2 | 11/2012 | Taylor et al. |
| 8,311,750 B2 | 11/2012 | Taylor |
| 8,315,812 B2 | 11/2012 | Taylor |
| 8,321,150 B2 | 11/2012 | Taylor |
| 8,331,314 B2 | 12/2012 | Quiang et al. |
| 8,496,594 B2 | 7/2013 | Taylor et al. |
| 8,523,779 B2 | 9/2013 | Taylor et al. |
| 8,548,778 B1 | 10/2013 | Hart et al. |
| 8,554,490 B2 | 10/2013 | Tang et al. |
| 8,560,968 B1 | 10/2013 | Nair |
| 8,768,669 B1 | 7/2014 | Hart et al. |
| 8,771,195 B2 | 7/2014 | Kim et al. |
| 8,787,641 B2 | 7/2014 | Hof et al. |
| 8,812,246 B2 | 8/2014 | Taylor |
| 8,824,752 B1 | 9/2014 | Fonte et al. |
| 8,837,860 B1 | 9/2014 | Grady et al. |
| 8,861,820 B2 | 10/2014 | Fonte et al. |
| 8,917,925 B1 | 12/2014 | Grady et al. |
| 8,970,578 B2 | 3/2015 | Voros et al. |
| 9,008,405 B2 | 4/2015 | Fonte et al. |
| 9,042,613 B2 | 5/2015 | Spilker et al. |
| 9,070,214 B1 | 6/2015 | Grady et al. |
| 9,078,564 B2 | 7/2015 | Taylor |
| 9,087,147 B1 | 7/2015 | Fonte |
| 9,129,418 B2 | 9/2015 | Schormans et al. |
| 9,138,147 B2 | 9/2015 | Schmitt et al. |
| 9,153,047 B1 | 10/2015 | Grady et al. |
| 9,189,600 B2 | 11/2015 | Spilker et al. |
| 9,256,936 B2 | 2/2016 | Jacobs et al. |
| 9,314,584 B1 | 4/2016 | Riley et al. |
| 9,375,191 B2 | 6/2016 | Verstraelen et al. |
| 9,406,141 B2 | 8/2016 | Kelm et al. |
| 9,430,827 B2 | 8/2016 | Kelm et al. |
| 9,466,117 B2 | 10/2016 | Habets et al. |
| 9,471,999 B2 | 10/2016 | Ishii et al. |
| 9,572,495 B2 | 2/2017 | Schmitt et al. |
| 9,576,360 B2 | 2/2017 | Schormans et al. |
| 9,613,186 B2 | 4/2017 | Fonte |
| 9,615,755 B2 | 4/2017 | Riley et al. |
| 9,633,454 B2 | 4/2017 | Lauritsch et al. |
| 9,646,361 B2 | 5/2017 | Koo et al. |
| 9,743,835 B2 | 8/2017 | Taylor |
| 9,754,082 B2 | 9/2017 | Taylor et al. |
| 9,786,068 B2 | 10/2017 | Ishii et al. |
| 9,814,433 B2 | 11/2017 | Benishti et al. |
| 9,858,387 B2 | 1/2018 | Lavi et al. |
| 9,870,634 B2 | 1/2018 | Grady et al. |
| 9,888,896 B2 | 2/2018 | Lauritsch et al. |
| 9,934,566 B2 | 4/2018 | Sun et al. |
| 9,940,736 B2 | 4/2018 | Ishii et al. |
| 9,943,233 B2 | 4/2018 | Lavi et al. |
| 9,965,873 B2 | 5/2018 | Grady et al. |
| 9,968,256 B2 | 5/2018 | Taokowsky et al. |
| 9,977,869 B2 | 5/2018 | Lavi et al. |
| 9,999,361 B2 | 6/2018 | Sharma et al. |
| 10,141,074 B2 | 11/2018 | Lavi et al. |
| 10,143,390 B2 | 12/2018 | Ledoux et al. |
| 10,159,529 B2 | 12/2018 | Taylor |
| 10,176,575 B2 | 1/2019 | Isgum et al. |
| 10,210,956 B2 | 2/2019 | Lavi et al. |
| 10,219,704 B2 | 3/2019 | Lavi et al. |
| 10,229,516 B2 | 3/2019 | Aben et al. |
| 10,235,796 B2 | 3/2019 | Aben et al. |
| 10,245,001 B2 | 4/2019 | Redel et al. |
| 10,342,442 B2 | 7/2019 | Hattangadi et al. |
| 10,354,744 B2 | 7/2019 | Sharma et al. |
| 10,360,674 B2 | 7/2019 | Contini et al. |
| 10,363,018 B2 | 7/2019 | Fukuda et al. |
| 10,373,700 B2 | 8/2019 | Sharma et al. |
| 10,376,165 B2 | 8/2019 | Lavi et al. |
| 10,395,366 B2 | 8/2019 | Isgum et al. |
| 10,395,774 B2 | 8/2019 | Lavi et al. |
| 10,420,610 B2 | 9/2019 | Bai et al. |
| 10,424,063 B2 | 9/2019 | Lavi et al. |
| 10,441,235 B2 | 10/2019 | Lavi et al. |
| 10,441,239 B2 | 10/2019 | Abe |
| 10,456,094 B2 | 10/2019 | Fonte et al. |
| 10,463,336 B2 | 11/2019 | Itu et al. |
| 10,470,730 B2 | 11/2019 | Benishti et al. |
| 10,559,388 B2 | 2/2020 | Lavi et al. |
| 10,580,526 B2 | 3/2020 | Ma et al. |
| 10,595,807 B2 | 3/2020 | Lavi et al. |
| 10,631,737 B2 | 4/2020 | Lavi et al. |
| 10,636,146 B2 | 4/2020 | Zhong et al. |
| 10,650,522 B2 | 5/2020 | Hoi et al. |
| 10,682,180 B2 | 6/2020 | Taylor |
| 10,699,407 B2 | 6/2020 | Isgum et al. |
| 10,733,792 B2 | 8/2020 | Aben et al. |
| 10,740,961 B2 | 8/2020 | Reiber et al. |
| 10,748,285 B2 | 8/2020 | Igarashi et al. |
| 10,758,200 B2 | 9/2020 | Passerini et al. |
| 10,776,988 B2 | 9/2020 | Grady et al. |
| 10,803,994 B2 | 10/2020 | Lavi et al. |
| 10,803,995 B2 | 10/2020 | Sharma et al. |
| 10,828,109 B2 | 11/2020 | Redel |
| 10,854,329 B2 | 12/2020 | Mohr et al. |
| 10,964,017 B2 | 3/2021 | Pack et al. |
| 10,964,071 B2 | 3/2021 | Grady et al. |
| 11,004,198 B2 | 5/2021 | Isgum et al. |
| 11,017,531 B2 | 5/2021 | Harish et al. |
| 11,031,136 B2 | 6/2021 | Grass et al. |
| 11,055,845 B2 | 7/2021 | Nickisch et al. |
| 11,076,770 B2 | 8/2021 | Lavi et al. |
| 11,081,237 B2 | 8/2021 | Lavi et al. |
| 11,083,377 B2 | 8/2021 | Bouwman et al. |
| 11,083,524 B2 | 8/2021 | Taylor |
| 11,087,884 B2 | 8/2021 | Sankaran et al. |
| 11,090,118 B2 | 8/2021 | Taylor |

(56) References Cited

U.S. PATENT DOCUMENTS

| | | |
|---|---|---|
| 11,116,575 B2 | 9/2021 | Taylor |
| 11,127,503 B2 | 9/2021 | Rabbat et al. |
| 11,138,733 B2 | 10/2021 | Lavi et al. |
| 11,141,123 B2 | 10/2021 | Homann et al. |
| 11,160,524 B2 | 11/2021 | Lavi et al. |
| 11,179,043 B2 | 11/2021 | Haase et al. |
| 11,185,368 B2 | 11/2021 | Spilker et al. |
| 11,195,278 B2 | 12/2021 | Nickisch et al. |
| 11,202,612 B2 | 12/2021 | Sakaguchi |
| 11,216,944 B2 | 1/2022 | Reiber et al. |
| 11,272,845 B2 | 3/2022 | Cheline et al. |
| 11,278,208 B2 | 3/2022 | Lavi et al. |
| 11,282,170 B2 | 3/2022 | Gauriau et al. |
| 11,288,811 B2 | 3/2022 | Tu et al. |
| 11,288,813 B2 | 3/2022 | Grady et al. |
| 11,295,864 B2 | 4/2022 | Benishti et al. |
| 11,298,187 B2 | 4/2022 | Taylor |
| 11,304,665 B2 | 4/2022 | Sharma et al. |
| 11,308,621 B2 | 4/2022 | Tu et al. |
| 11,328,824 B2 | 5/2022 | Fonte |
| 11,341,631 B2 | 5/2022 | Song et al. |
| 11,375,904 B2 | 7/2022 | Igarashi |
| 11,382,569 B2 | 7/2022 | Grady et al. |
| 11,389,130 B2 | 7/2022 | Itu et al. |
| 11,398,029 B2 | 7/2022 | Grady et al. |
| 11,406,337 B2 | 8/2022 | Lavi et al. |
| 11,406,339 B2 | 8/2022 | Mistretta et al. |
| 11,409,422 B2 | 8/2022 | Olivan Bescos et al. |
| 11,410,308 B2 | 8/2022 | Gulsun et al. |
| 11,423,532 B2 * | 8/2022 | Takahashi ............ A61B 5/0215 |
| 11,424,036 B2 | 8/2022 | Fonte et al. |
| 11,424,038 B2 | 8/2022 | Grady et al. |
| 11,443,428 B2 | 9/2022 | Petersen et al. |
| 11,445,923 B2 | 9/2022 | Tu et al. |
| 11,462,326 B2 | 10/2022 | Wang et al. |
| 11,462,329 B2 | 10/2022 | Rabbat et al. |
| 11,468,567 B2 | 10/2022 | Groth et al. |
| 11,482,339 B2 | 10/2022 | Koo et al. |
| 11,490,867 B2 | 11/2022 | Homann et al. |
| 11,494,904 B2 | 11/2022 | Fonte et al. |
| 11,501,485 B2 | 11/2022 | Grady et al. |
| 11,508,460 B2 | 11/2022 | Wang et al. |
| 11,510,587 B2 | 11/2022 | Kristanto et al. |
| 11,521,755 B2 | 12/2022 | Taylor et al. |
| 11,523,744 B2 | 12/2022 | Freiman et al. |
| 11,538,161 B2 | 12/2022 | Wang et al. |
| 11,540,931 B2 | 1/2023 | Grady et al. |
| 11,557,036 B2 | 1/2023 | Liao et al. |
| 11,557,069 B2 | 1/2023 | Senzig et al. |
| 11,559,274 B2 | 1/2023 | Auvray et al. |
| 11,564,746 B2 | 1/2023 | Spilker et al. |
| 11,564,748 B2 | 1/2023 | Thienphrapa et al. |
| 11,574,406 B2 | 2/2023 | Chen et al. |
| 11,576,621 B2 | 2/2023 | Sharma et al. |
| 11,576,626 B2 | 2/2023 | Fonte et al. |
| 11,576,637 B2 | 2/2023 | Schmitt et al. |
| 11,576,639 B2 | 2/2023 | Song et al. |
| 11,583,340 B2 | 2/2023 | Taylor |
| 11,589,924 B2 | 2/2023 | Passerini et al. |
| 11,599,996 B2 | 3/2023 | Isgum et al. |
| 11,607,189 B2 | 3/2023 | Tu et al. |
| 11,610,309 B2 | 3/2023 | Kweon et al. |
| 11,610,318 B2 | 3/2023 | Grady et al. |
| 11,615,894 B2 | 3/2023 | Lavi et al. |
| 11,617,620 B2 | 4/2023 | Tran et al. |
| 11,633,118 B2 | 4/2023 | Freiman et al. |
| 11,638,609 B2 | 5/2023 | Sankaran et al. |
| 11,642,171 B2 | 5/2023 | Jaquet et al. |
| 11,653,833 B2 | 5/2023 | Sanders et al. |
| 11,664,128 B2 | 5/2023 | Haase et al. |
| 11,688,502 B2 | 6/2023 | Anderson et al. |
| 11,690,518 B2 | 7/2023 | Haase et al. |
| 11,694,339 B2 | 7/2023 | Schormans et al. |
| 11,707,196 B2 | 7/2023 | Lavi et al. |
| 11,707,242 B2 | 7/2023 | Van Walsum et al. |
| 11,710,569 B2 | 7/2023 | Grass et al. |
| 11,728,037 B2 | 8/2023 | Lavi et al. |
| 11,741,574 B2 | 8/2023 | Kweon et al. |
| 11,741,602 B2 | 8/2023 | Reiber et al. |
| 11,744,472 B2 | 9/2023 | Zhao et al. |
| 11,744,544 B2 | 9/2023 | Sheehan et al. |
| 11,748,902 B2 | 9/2023 | Bai et al. |
| 11,756,195 B2 | 9/2023 | Kweon et al. |
| 11,769,254 B2 | 9/2023 | Song et al. |
| 11,776,149 B2 | 10/2023 | Wang et al. |
| 11,779,225 B2 | 10/2023 | Adiyoso |
| 11,779,233 B2 | 10/2023 | Huo et al. |
| 11,779,294 B2 | 10/2023 | Liu et al. |
| 11,786,202 B2 | 10/2023 | Yin et al. |
| 11,793,575 B2 | 10/2023 | Taylor |
| 11,803,966 B2 | 10/2023 | Denzinger et al. |
| 11,810,290 B2 | 11/2023 | Flohr et al. |
| 11,810,661 B2 | 11/2023 | Barley et al. |
| 11,816,836 B2 | 11/2023 | Isgum et al. |
| 11,816,837 B2 | 11/2023 | Lavi et al. |
| 11,826,106 B2 | 11/2023 | Hart et al. |
| 11,826,175 B2 | 11/2023 | Itu et al. |
| 11,847,547 B2 | 12/2023 | Wang et al. |
| 2003/0105401 A1 | 6/2003 | Jago et al. |
| 2004/0019264 A1 | 1/2004 | Suurmond et al. |
| 2004/0066958 A1 | 4/2004 | Chen et al. |
| 2005/0043614 A1 | 2/2005 | Huizenga et al. |
| 2005/0249327 A1 | 11/2005 | Wink et al. |
| 2005/0272992 A1 * | 12/2005 | O'Donnell ................ G06T 7/12 600/407 |
| 2006/0036167 A1 | 2/2006 | Shina |
| 2006/0084862 A1 | 4/2006 | Suurmond et al. |
| 2007/0031019 A1 | 2/2007 | Lesage et al. |
| 2007/0167833 A1 | 7/2007 | Redel et al. |
| 2008/0020362 A1 | 1/2008 | Cotin et al. |
| 2008/0187199 A1 | 8/2008 | Gulsun et al. |
| 2008/0205722 A1 | 8/2008 | Schaefer et al. |
| 2009/0016483 A1 | 1/2009 | Kawasaki et al. |
| 2009/0171321 A1 | 7/2009 | Callaghan |
| 2009/0312648 A1 | 12/2009 | Zhang et al. |
| 2010/0010428 A1 | 1/2010 | Yu et al. |
| 2010/0017171 A1 | 1/2010 | Spilker et al. |
| 2010/0021025 A1 | 1/2010 | Hof et al. |
| 2010/0067760 A1 | 3/2010 | Zhang et al. |
| 2010/0125197 A1 | 5/2010 | Fishel |
| 2010/0160764 A1 | 6/2010 | Steinberg et al. |
| 2010/0220917 A1 | 9/2010 | Steinberg et al. |
| 2010/0296709 A1 | 11/2010 | Ostrovsky-Berman et al. |
| 2010/0298719 A1 | 11/2010 | Thrysoe et al. |
| 2011/0015530 A1 | 1/2011 | Misawa |
| 2011/0096907 A1 | 4/2011 | Mohamed |
| 2011/0134433 A1 | 6/2011 | Yamada |
| 2011/0135175 A1 | 6/2011 | Ostrovsky-Berman et al. |
| 2011/0142313 A1 | 6/2011 | Pack et al. |
| 2011/0182492 A1 | 7/2011 | Grass et al. |
| 2012/0014574 A1 * | 1/2012 | Ferschel ................ G06T 7/0012 382/128 |
| 2012/0041318 A1 | 2/2012 | Taylor |
| 2012/0041739 A1 | 2/2012 | Taylor |
| 2012/0053918 A1 | 3/2012 | Taylor |
| 2012/0053919 A1 | 3/2012 | Taylor |
| 2012/0053921 A1 | 3/2012 | Taylor |
| 2012/0059246 A1 | 3/2012 | Taylor |
| 2012/0059249 A1 * | 3/2012 | Verard ................... A61B 6/463 600/424 |
| 2012/0062841 A1 | 3/2012 | Stetson et al. |
| 2012/0072190 A1 | 3/2012 | Sharma et al. |
| 2012/0150048 A1 | 6/2012 | Kang et al. |
| 2012/0177275 A1 | 7/2012 | Suri |
| 2012/0230565 A1 | 9/2012 | Steinberg et al. |
| 2012/0236032 A1 | 9/2012 | Arvidsson |
| 2012/0243761 A1 | 9/2012 | Senzig et al. |
| 2013/0060133 A1 | 3/2013 | Kassab et al. |
| 2013/0094745 A1 | 4/2013 | Sundar |
| 2013/0158476 A1 | 6/2013 | Olson |
| 2013/0226003 A1 | 8/2013 | Edic et al. |
| 2013/0229621 A1 | 9/2013 | Stetson et al. |
| 2013/0324842 A1 | 12/2013 | Mittal et al. |
| 2014/0005535 A1 | 1/2014 | Edic et al. |

(56) References Cited

U.S. PATENT DOCUMENTS

| | | |
|---|---|---|
| 2014/0086461 A1 | 3/2014 | Yao et al. |
| 2014/0094693 A1 | 4/2014 | Cohen et al. |
| 2014/0100451 A1 | 4/2014 | Tolkowsky et al. |
| 2014/0121513 A1 | 5/2014 | Tolkowsky et al. |
| 2014/0142398 A1 | 5/2014 | Patil et al. |
| 2014/0200867 A1 | 7/2014 | Lavi et al. |
| 2014/0303495 A1 | 10/2014 | Fonte et al. |
| 2014/0371578 A1 | 12/2014 | Auvray et al. |
| 2015/0201897 A1 | 7/2015 | Kyriakou |
| 2015/0250395 A1 | 9/2015 | Igarashi |
| 2015/0265162 A1 | 9/2015 | Lavi et al. |
| 2015/0302578 A1 | 10/2015 | Grady et al. |
| 2015/0335304 A1 | 11/2015 | Lavi et al. |
| 2015/0339847 A1 | 11/2015 | Benishti et al. |
| 2015/0342551 A1 | 12/2015 | Lavi et al. |
| 2016/0007945 A1 | 1/2016 | Taylor |
| 2016/0022371 A1 | 1/2016 | Sauer et al. |
| 2016/0073928 A1* | 3/2016 | Soper .................. A61B 5/08 600/424 |
| 2016/0110866 A1 | 4/2016 | Taylor |
| 2016/0110867 A1 | 4/2016 | Taylor |
| 2016/0128661 A1 | 5/2016 | Taylor |
| 2016/0157802 A1 | 6/2016 | Anderson |
| 2016/0228000 A1 | 8/2016 | Spaide |
| 2016/0247279 A1 | 8/2016 | Lavi et al. |
| 2016/0371456 A1 | 12/2016 | Taylor et al. |
| 2017/0018116 A1 | 1/2017 | Sun et al. |
| 2017/0039736 A1 | 2/2017 | Aben et al. |
| 2017/0224418 A1 | 8/2017 | Boettner et al. |
| 2017/0286628 A1 | 10/2017 | Shim |
| 2017/0325770 A1 | 11/2017 | Edic et al. |
| 2018/0032653 A1 | 2/2018 | Aben et al. |
| 2018/0075221 A1 | 3/2018 | Vergaro et al. |
| 2018/0089829 A1 | 3/2018 | Zhong et al. |
| 2018/0182096 A1 | 6/2018 | Grady et al. |
| 2018/0211386 A1 | 7/2018 | Ma et al. |
| 2018/0235561 A1 | 8/2018 | Lavi et al. |
| 2018/0243033 A1 | 8/2018 | Tran et al. |
| 2018/0268941 A1 | 9/2018 | Lavi et al. |
| 2018/0315193 A1 | 11/2018 | Paschalakis et al. |
| 2018/0330507 A1 | 11/2018 | Schormans et al. |
| 2018/0344173 A1 | 12/2018 | Tu et al. |
| 2018/0344174 A9 | 12/2018 | Schmitt et al. |
| 2019/0005737 A1 | 1/2019 | Auvray et al. |
| 2019/0019347 A1 | 1/2019 | Auvray et al. |
| 2019/0130578 A1* | 5/2019 | Gulsun ............... G06N 3/045 |
| 2019/0282199 A1 | 9/2019 | Merritt |
| 2020/0126229 A1 | 4/2020 | Lavi et al. |
| 2020/0138521 A1 | 5/2020 | Aben et al. |
| 2020/0160509 A1 | 5/2020 | Pack et al. |
| 2020/0222018 A1 | 7/2020 | van Walsum et al. |
| 2020/0265958 A1 | 8/2020 | Haase et al. |
| 2020/0337664 A1 | 10/2020 | Homann et al. |
| 2020/0394795 A1 | 12/2020 | Isgum et al. |
| 2021/0022617 A1 | 1/2021 | Zhao et al. |
| 2021/0035290 A1 | 2/2021 | Aben et al. |
| 2021/0244475 A1 | 8/2021 | Taylor |
| 2021/0259559 A1 | 8/2021 | Tu et al. |
| 2021/0267690 A1 | 9/2021 | Taylor |
| 2021/0272030 A1 | 9/2021 | Sankaran et al. |
| 2021/0275124 A1 | 9/2021 | Huo et al. |
| 2021/0280318 A1 | 9/2021 | Huo et al. |
| 2021/0282731 A1 | 9/2021 | Vaillant et al. |
| 2021/0282860 A1 | 9/2021 | Taylor |
| 2021/0290308 A1 | 9/2021 | Mihalef et al. |
| 2021/0298706 A1 | 9/2021 | Tu et al. |
| 2021/0298708 A1 | 9/2021 | Aben et al. |
| 2021/0334963 A1 | 10/2021 | Isgum et al. |
| 2021/0338088 A1 | 11/2021 | Bouwman et al. |
| 2021/0345889 A1 | 11/2021 | Tu et al. |
| 2021/0358634 A1 | 11/2021 | Sankaran et al. |
| 2021/0361174 A1 | 11/2021 | Lavi et al. |
| 2021/0361176 A1 | 11/2021 | Huo et al. |
| 2021/0374950 A1 | 12/2021 | Gao et al. |
| 2021/0375474 A1 | 12/2021 | Lavi et al. |
| 2021/0383539 A1 | 12/2021 | Haase et al. |
| 2021/0401400 A1 | 12/2021 | Sheehan et al. |
| 2022/0012876 A1 | 1/2022 | Sommer et al. |
| 2022/0015730 A1 | 1/2022 | Haase et al. |
| 2022/0028080 A1 | 1/2022 | Lavi et al. |
| 2022/0036646 A1 | 2/2022 | Song et al. |
| 2022/0039769 A1 | 2/2022 | M et al. |
| 2022/0047236 A1 | 2/2022 | Lavi et al. |
| 2022/0054022 A1 | 2/2022 | Van Lavieren et al. |
| 2022/0079455 A1 | 3/2022 | Haase et al. |
| 2022/0079540 A1 | 3/2022 | Sankaran et al. |
| 2022/0079563 A1 | 3/2022 | Kemp |
| 2022/0087544 A1 | 3/2022 | Schmitt et al. |
| 2022/0092775 A1 | 3/2022 | Denzinger et al. |
| 2022/0092784 A1 | 3/2022 | Tu et al. |
| 2022/0101535 A1 | 3/2022 | Thamm et al. |
| 2022/0110687 A1 | 4/2022 | Spilker et al. |
| 2022/0151580 A1 | 5/2022 | Itu et al. |
| 2022/0164953 A1 | 5/2022 | Gulsun et al. |
| 2022/0167938 A1 | 6/2022 | Grass et al. |
| 2022/0172368 A1 | 6/2022 | Lavi et al. |
| 2022/0183655 A1 | 6/2022 | Huang et al. |
| 2022/0211280 A1 | 7/2022 | Lavi et al. |
| 2022/0211439 A1 | 7/2022 | Sankaran et al. |
| 2022/0230312 A1 | 7/2022 | Choi et al. |
| 2022/0233081 A1 | 7/2022 | Cheline et al. |
| 2022/0254028 A1 | 8/2022 | Liu et al. |
| 2022/0261997 A1 | 8/2022 | Liu et al. |
| 2022/0262000 A1 | 8/2022 | Haase et al. |
| 2022/0273180 A1 | 9/2022 | Lavi et al. |
| 2022/0277447 A1 | 9/2022 | Wang et al. |
| 2022/0285034 A1 | 9/2022 | Lavi et al. |
| 2022/0319004 A1 | 10/2022 | Bruch-el et al. |
| 2022/0319116 A1 | 10/2022 | Wang et al. |
| 2022/0335612 A1 | 10/2022 | Bruch-El et al. |
| 2022/0351369 A1 | 11/2022 | Haase et al. |
| 2022/0415510 A1 | 12/2022 | Wang et al. |
| 2023/0037338 A1 | 2/2023 | Wang et al. |
| 2023/0038364 A1 | 2/2023 | Bhowmick et al. |
| 2023/0084748 A1 | 3/2023 | Lavi et al. |
| 2023/0108647 A1 | 4/2023 | Tu et al. |
| 2023/0113721 A1 | 4/2023 | Kassel et al. |
| 2023/0144795 A1 | 5/2023 | Wang et al. |
| 2023/0148977 A1 | 5/2023 | Fonte et al. |
| 2023/0186472 A1 | 6/2023 | Kweon et al. |
| 2023/0196582 A1 | 6/2023 | Grady et al. |
| 2023/0197286 A1 | 6/2023 | Grady et al. |
| 2023/0230235 A1 | 7/2023 | Isgum et al. |
| 2023/0237652 A1 | 7/2023 | Flexman et al. |
| 2023/0245301 A1 | 8/2023 | Wang et al. |
| 2023/0252628 A1 | 8/2023 | Haase et al. |
| 2023/0263401 A1 | 8/2023 | Escaned-Barbosa et al. |
| 2023/0277247 A1 | 9/2023 | Taylor et al. |
| 2023/0282365 A1 | 9/2023 | Lavi et al. |
| 2023/0298176 A1 | 9/2023 | Choi et al. |
| 2023/0309943 A1 | 10/2023 | van Walsum et al. |
| 2023/0320789 A1 | 10/2023 | Bai et al. |
| 2023/0326127 A1 | 10/2023 | Zhong et al. |
| 2023/0334659 A1 | 10/2023 | Kuo et al. |
| 2023/0346236 A1 | 11/2023 | Lavi et al. |
| 2023/0352152 A1 | 11/2023 | Grady et al. |
| 2023/0355107 A1 | 11/2023 | Haase et al. |
| 2023/0360803 A1 | 11/2023 | Sankaran et al. |
| 2023/0386037 A1 | 11/2023 | Denzinger et al. |
| 2023/0404525 A1 | 12/2023 | Sheehan et al. |
| 2024/0029529 A1 | 1/2024 | Scalisi |

FOREIGN PATENT DOCUMENTS

| | | |
|---|---|---|
| CN | 113837985 | 12/2021 |
| EP | 1396274 | 3/2004 |
| EP | 2163272 | 3/2010 |
| EP | 2633815 A1 | 9/2013 |
| EP | 2779907 | 9/2014 |
| EP | 2873371 | 5/2015 |
| EP | 3125764 | 2/2017 |
| EP | 2633815 B1 | 6/2017 |
| EP | 3363350 | 8/2018 |
| EP | 3460688 | 3/2019 |

(56) References Cited

FOREIGN PATENT DOCUMENTS

| | | |
|---|---|---|
| EP | 3477551 | 5/2019 |
| EP | 3763285 | 1/2021 |
| EP | 3847956 | 7/2021 |
| EP | 2776960 | 9/2021 |
| EP | 3534372 | 9/2021 |
| EP | 3871184 | 9/2021 |
| EP | 3881758 | 9/2021 |
| EP | 3884868 | 9/2021 |
| EP | 3282380 | 11/2021 |
| EP | 3282381 | 11/2021 |
| EP | 3903672 | 11/2021 |
| EP | 3912139 | 11/2021 |
| EP | 3664026 | 2/2022 |
| EP | 3945469 | 2/2022 |
| EP | 3949860 | 2/2022 |
| EP | 3951705 | 2/2022 |
| EP | 3076854 | 4/2022 |
| EP | 3979259 | 4/2022 |
| EP | 3258446 | 5/2022 |
| EP | 4026143 | 7/2022 |
| EP | 4026491 | 7/2022 |
| EP | 4026492 | 7/2022 |
| EP | 4029438 | 7/2022 |
| EP | 3298959 | 9/2022 |
| EP | 3989828 | 11/2022 |
| EP | 3157411 | 12/2022 |
| EP | 3606437 | 12/2022 |
| EP | 4104765 | 12/2022 |
| EP | 4131150 | 2/2023 |
| EP | 4145391 | 3/2023 |
| EP | 3169237 | 4/2023 |
| EP | 4160528 | 4/2023 |
| EP | 3403582 | 6/2023 |
| EP | 3743883 | 6/2023 |
| EP | 3989832 | 8/2023 |
| EP | 3652747 | 9/2023 |
| EP | 4104766 | 9/2023 |
| EP | 3602485 | 10/2023 |
| EP | 4064181 | 11/2023 |
| EP | 3602487 | 12/2023 |
| JP | H08-131429 | 5/1996 |
| JP | 2003-508152 | 3/2003 |
| JP | 2003-514600 | 4/2003 |
| JP | 2004-243117 | 9/2004 |
| JP | 2007-502644 | 2/2007 |
| JP | 2007-325920 | 12/2007 |
| JP | 4177217 B2 | 11/2008 |
| JP | 2010-042247 | 2/2010 |
| JP | 2011-212314 | 10/2011 |
| JP | 2013-090799 | 5/2013 |
| JP | 2010-505493 | 7/2013 |
| JP | 2013-534154 | 9/2013 |
| JP | 2014-064915 | 4/2014 |
| JP | 2015-503416 | 2/2015 |
| JP | 2015-527901 | 9/2015 |
| NL | 2012324 | 8/2015 |
| WO | WO 2001/21057 | 3/2001 |
| WO | WO 2007/066249 | 6/2007 |
| WO | WO 2010/033971 | 3/2010 |
| WO | WO 2011/038044 | 3/2011 |
| WO | WO 2012/021037 | 2/2012 |
| WO | WO 2012/021307 | 2/2012 |
| WO | WO 2012/173697 | 12/2012 |
| WO | WO 2014/027692 | 2/2014 |
| WO | WO 2014/064702 | 5/2014 |
| WO | WO 2014/111927 | 7/2014 |
| WO | WO 2014/111929 | 7/2014 |
| WO | WO 2014/111930 | 7/2014 |
| WO | WO 2015/059706 | 4/2015 |
| WO | WO 2017/199245 | 11/2017 |
| WO | WO 2017/199246 | 11/2017 |
| WO | WO 2018/165478 | 9/2018 |
| WO | WO 2020/053099 | 3/2020 |
| WO | WO 2020/084101 | 4/2020 |
| WO | WO 2020/201942 | 10/2020 |
| WO | WO 2021/016071 | 1/2021 |
| WO | 2021/059165 A1 | 4/2021 |
| WO | WO 2021/175039 | 9/2021 |
| WO | WO 2021/191909 | 9/2021 |
| WO | WO 2021/258835 | 12/2021 |
| WO | WO 2022/000727 | 1/2022 |
| WO | WO 2022/000729 | 1/2022 |
| WO | WO 2022/000733 | 1/2022 |
| WO | WO 2022/000734 | 1/2022 |
| WO | WO 2022/000976 | 1/2022 |
| WO | WO 2022/000977 | 1/2022 |
| WO | WO 2022/002765 | 1/2022 |
| WO | WO 2022/069208 | 4/2022 |

OTHER PUBLICATIONS

International Search Report and Written Opinion, dated Dec. 15, 2020, for International Application Serial No. PCT/IB2020/058901 filed Sep. 23, 2020.
Abraham et al., "Alternative routes in road networks", ACM Journal of Experimental Algorithmics, Association of Computing Machinery, vol. 18(1):1.3:2-1.3:17 (2013).
Andriotis et al., "A new method of three-dimensional coronary artery reconstruction from X-Ray angiography: Validation against a virtual phantom and multislice computed tomography", Catheterization and Cardiovascular Interventions, vol. 71:28-43 (2008).
Barnea, "Model-based estimation of coronary vessel diameter in angiographic images", Proceedings of the 20th Annual International Conference of the IEEE Engineering in Medicine and Biology Society, vol. 20:513-516 (1998).
Barratt et al., "Reconstruction and quantification of the carotid artery bifurcation from 3-D ultrasound images", IEEE Transactions on Medical Imaging, vol. 23(5):567-583 (2004).
Bullitt et al., "Determining malignancy of brain tumors by analysis of vessel shape", Medical Image Computing and Computer-Assisted Intervention, MICCAI 2004 Conference Proceedings, Lecture notes in Computer Science, LNCS, 3217:645-653.
Caiati et al., "New noninvasive method for coronary flow reserve assessment: Contrast-enhanced transthoracic second harmonic echo doppler", Circulation, vol. 99:771-778 (1999).
Caiati et al., "Detection, location, and severity assessment of left anterior descneding coronary artery stenoses by means of contrast-enhanced transthoracic harmonic echo dopper", European Heart Journal, vol. 30:1797-1806 (2009).
Chung, "Image segmentation methods for detecting blood vessels in angiography", 2006 9th International Conference on Control, Automation, Robotics and Vision, Singapore, pp. 1-6 (2006).
Dickie et al., "Live-vessel: interactive vascular image segmentation with simultaneous extraction of optimal medial and boundary paths", Technical Report TR 2009-23, School of Computing Science, Simon Fraser University, Burnaby, BC, Canada, Nov. 2009.
Frangi et al., "Multiscale vessel and enhancement filtering", Medical Image Computing and Computer-Assisted Intervention, MICCA '98 Lecture Notes in Computer Science, vol. 1496:130-137 (1998).
Fraz, "Blood vessel segmentation methodologies, in retinal images—a survey", Computer Methods and Programs in Biomedicine, vol. 108:407-433 (2012).
Fusejima, "Noninvasive measurement of coronary artery blood flow using combined two-dimensional and doppler echocardiography", JACC vol. 10(5):1024-1031 (1987).
Hawkes et al., "Validation of volume blood flow measurements using three-dimensional distance-concentration functions detived from digital X-Ray angiograms", Investigative Radiology, vol. 29(4):434-442 (1994).
Hoffmann et al., "Determination of instantaneous and average blood flow rates from digital angiograms of vessel phantoms using distance-density curves", Investigative Radiology, vol. 26(3):207-212 (1991).
Holdsworth et al., "Quantitative angiographic blood-flow measurement using pulsed intra-arterial injection", Medical Physics, vol. 26(10):2168-2175 (1999).
Huo et al., "Intraspecific scaling laws of vascular trees", J.R. Soc. Interface vol. 9:190-200 (2012).

(56) References Cited

OTHER PUBLICATIONS

Janssen et al., "New approaches for the assessment of vessel sizes in quantitative (cardio-)vascular X-ray analysis", Int J Cardiovasc Imaging vol. 26:259-271 (2010).
Kappetein et al., "Current percutaneous coronary intervention and coronary artery bypass grafting practices for three-vessel and left main coronary artery disease: Insights from the SYNTAX run-in phase", European Journal of Cardio-Thoracic Surgery, vol. 29:486-491 (2010).
Kass et al., "Snakes: active contour models", Int. J. Comput. Vis. vol. 1:321-331 (1987).
Kirkeeide, "Coronary obstructions, morphology and physiologic significance", Quantitative Coronary Arteriography, Chap. 11:229-244 (1991).
Lethen et al., "Validation of noninvasive assessment of coronary flow velocity reserve in the right coronary artery—a comparison of transthoracic echocardiographic results with intracoronary doppler flow wire measurements", European Heart Journal, vol. 24:1567-1575 (2003).
Li et al., "Minimization of region-scalable fitting energy for image segmentation", in IEEE Transactions on Image Processing, vol. 17(10):1940-1949 (2008).
Meimoun et al., "Non-invasive assessment of coronary flow and coronary flow reserve by transthoracic doppler echocardiography: a magic tool for the real world", European Journal of Echocardiography, vol. 9:449-457 (2008).
Mercer-Rosa et al., "Illustration of the additional value of real-time 3-dimensional echocardiography to conventional transthoracic and transesophageal 2-dimensional echocardiography in imaging muscular ventricular septal defects: does this have any impact on individual patient treatment", Journal of the American Society of Echocardiography, vol. 19(12):1511-1519 (2006).
Molloi et al., "Quantification of fractional flow reserve using angiographic image data", World Congress on Medical Physics and Biomedical Engineering, Munich, Germany, Sep. 7-12, 2009.
Molloi et al., "Estimation of coronary artery hyperemic blood flow based on arterial lumen vol. using angiographic images", Int J Cardiovasc Imaging, vol. 28:1-11 (2012).
Ng et al., "Novel QCA methodologies and angiographic scores", Int J Cardiovasc Imaging vol. 27:157-165 (2011).
Pellot et al., "A 3D reconstruction of vascular structures from two X-Ray angiograms using an adapted simulated annealing algorithm", IEEE Transactions of Medical Imaging, vol. 13(1):48-60 (1994).
Pinho et al., "Assessment and stenting of tracheal stenosis using deformable shape models", Medical Image Analysis, vol. 15(2):250-266 (2010).
Polytimi et al., "Close to transplant renal artery stenosis and percutaneous transluminal treatment", Journal of Transplantation, vol. 2011, 7 pages (2011).
Sarwal et al., "3-D reconstruction of coronary arteries", Proceedings of the 16th Annual Intl. Conference of the IEEE Engineering in Medicine and Biology Society, Engineering Advances: New Opportunities for Biomedical Engineers, Nov. 3, 1994, pp. 504-505.
Sato et al., "A viewpoint determination system for stenosis diagnosis and quantification in coronary angiogrphic image acquisition", IEEE Transactions on Medical Imaging, vol. 17(1):121-137 (1998).
Seifalian et al., "A new algorithm for deriving pulsatile blood flow waveforms tested using simulated dynamic angiographic data", Neuroradiology, vol. 31:263-269 (1989).
Seifalian et al., "Blood flow measurements using 3D distance-concentration functions derived from digital x-ray angiograms", Cardiovascular Imaging, Chap. 33:425-442 (1996).
Seifalian et al., "Validation of a quantitative radiographic technique to estimate pulsatile blood flow waveforms using digital subtraction angiographic data", Journal of Biomedical Engineering, vol. 13(3):225-233 (1991).

Shang et al., "Vascular active contour for vessel tree segmentation", in IEEE Transactions on Biomedical Engineering, vol. 58(4):1023-1032 (2011).
Shpilfoygel et al., "Comparison of methods for instantaneous angiographic blood flow measurement", Medical Physics, vol. 26(6):862-871 (1999).
Sianos et al., "The SYNTAX score: an angiographic tool grading the complexity of coronary artery disease", Euro Intervention, vol. 1(2):219-227 (2005).
Siogkas et al., "Quantification of the effect of percutaneous coronary angioplasty on a stenosed right coronary artery", 2010 10th IEEE Intl. Conference on Information Technology and Applications in Biomedicine, Nov. 3-5, 210, pp. 1-4 (2010).
Slomka et al., "Fully automated wall motion and thickening scoring system for myocardial perfusion SPECT: Method development and validation in large population", Journal of Nuclear Cardiology, vol. 19(2):291-302 (2012).
Sprague et al., "Coronary x-ray angiographic reconstruction and image orientation", Medical Physics, vol. 33(3):707-718 (2006).
Sun et al., "Coronary CT angiography: current status and continuing challenges", The British Journal of Radiology, vol. 85:495-510 (2012).
Takarada et al., "An angiographic technique for coronary fractional flow reserve measurement: in vivo validation", International Journal of Cardiovascular Imaging, published online pp. 1-10, Aug. 31, 2012.
Termeer et al., "Visualization of myocardial perfusion derived from coronary anatomy", IEEE Transactions on Visualization and Computer Graphics, vol. 14(6):1595-1602 (2008).
Tomasello et al., "Quantitative coronary angiography in the interventional cardiology", Advances in the Diagnosis of Coronary Atherosclerosis, Chap. 14:255-272 (2011).
Tu et al., Assessment of obstruction length and optimal viewing angle from biplane X-ray angiograms, Int J Cardiovasc Imaging, vol. 26:5-17 (2010).
Tu et al., "In vivo assessment of optimal viewing angles from X-ray coronary angiography", EuroIntervention, vol. 7:112-120 (2011).
Tu et al., "In vivo assessment of bifurcation optimal viewing angles and bifurcation angles by three-dimentional (3D) quantitative coronary angiography", Int J Cardiovasc Imaging, published online Dec. 15, 2011, in 9 pages.
Tu et al., "The impact of acquisition angle differences on three-dimensional quantitative coronary angiography", Catheterization and Cardiovascular Interventions, vol. 78:214-222 (2011).
Tuinenburg et al., "Dedicated bifurcation analysis: basic principles", Int J Cardiovasc Imaging, vol. 27:167-174 (2001).
Voci et al., "Coronary flow: a new asset for the echo lab?", European Heart Journal, vol. 25:1867-1879 (2004).
Weickert et al., "A scheme for coherence-enhancing diffusion filtering with optimized rotation invariance", Computer Vision, Graphics, and Pattern Recognition Group, Technical Report, Computer Science Series, pp. 1-20 (2000).
Weickert, "Anisotropic diffusion in image processing", ECMI, published by Teubner Stuttgart, Germany, 181 pages (2008).
Weickert et al., "A scheme for coherence-enhancing diffusion filtering with optimized rotation invariance", Journal of Visual Communication and Image Representation, vol. 13(1-2):103-118 (2002).
Wong et al., "Quantification of fractional flow reserve based on angiographic image data", The International Journal of Cardiac Imaging, vol. 28(1):13-22 (2012).
Wong et al., "Determination of fractional flow reserve (FFR) based on scaling laws: a simulation study", Physics in Medicine and Biology, vol. 53:3995-4011 (2008).
Wong et al., "Automated technique for angiographic determination of coronary blood flow and lumen volume", Acad. Radiol. vol. 13:186-194 (2006).
Xu et al., "Snakes, shapes, and gradient vector flow", IEEE Transactions on Image Processing, vol. 7:359-369 (1998).
Yang et al., "Novel approach for 3-D reconstruction of coronary arteries from two uncalibrated angiographic images", IEEE Transactions on Image Processing, vol. 18(7):1563-1572 (2009).

(56) References Cited

OTHER PUBLICATIONS

Youssef et al., "Role of computed tomography coronary angiography in the detection of vulnerable plaque, where does it stand among others?", Angiology, vol. 1(2):1000111-1-1000111-8 (2013).

Zhang et al., "Quantification of coronary microvascular resistance using angiographic images for volumetric blood flow measurement: in vivo validation", Am J Physio Heart Circ vol. 300(6):H2096-H2104 (2011).

Barrett et al., "Interactive live-wire 1-3 boundary extraction", Medical Image Analysis, Oxford University Press, vol. 1(4):331-341 (1997).

Jiang et al., "Vascular tree reconstruction by minimizing a physiological functional cost", 2010 IEEE Computer Society Conference on Computer Vision and Pattern Recognition—workshops, San Francisco, CA, pp. 178-185, doi: 10.1109/CVPRW.2010.5543593.

Marchenko, et al., "Vascular editor: from angiographic images to 3D vascular models", Journal of Digital Imaging, vol. 23:386-398 (2010).

Rabbat et al., "Interpreting results of coronary computed tomography angiography-derived fractional flow reserve in clinical practice", Journal of Cardiovascular Computed Tomography, vol. 11(5):1-6 (2017).

Wang et al., "Optimal viewing angle determination for multiple vessel segments in coronary angiographic image", IEEE Transactions on Nuclear Science, vol. 61(3):1290-1303 (2014).

Wang et al., "Global optimization angiographic viewing angles for coronary arteries with multiple segments", 35th Annual International Conference of the IEEE EMBS, pp. 2640-2643, Osaka, Japan, Jul. 3-7, 2013.

Office Action in European Application No. 20781104.3, dated Sep. 4, 2023, in 5 pages.

\* cited by examiner

| ROA_1° = ROLL +1° | CRANIAL_1° = PITCH -1° |
| ROA_2° = ROLL +2° | CRANIAL_2° = PITCH -2° |
| ROA_4° = ROLL +5° | CRANIAL_4° = PITCH -4.5° |
| ROA_10° = ROLL +12° | CRANIAL_10° = PITCH -11° |
| LOA_1° = ROLL -1° | CAUDAL_1° = PITCH +1° |
| LOA_2° = ROLL -2° | CAUDAL_2° = PITCH +2° |
| LOA_4° = ROLL -5° | CAUDAL_4° = PITCH +4.5° |
| LOA_10° = ROLL -12° | CAUDAL_10° = PITCH +11° |

PROCESSOR 30

METHODS, APPARATUS, AND SYSTEM FOR SYNCHRONIZATION BETWEEN A THREE-DIMENSIONAL VASCULAR MODEL AND AN IMAGING DEVICE

PRIORITY CLAIM

The present application is a national phase filing of International Application No. PCT/IB2020/058901, filed on Sep. 23, 2020, which claims priority to U.S. Provisional Patent Application No. 62/904,147, filed on Sep. 23, 2019, the entire contents of each of which are incorporated herein by reference and relied upon.

TECHNICAL FIELD

The present invention, in some embodiments thereof, relates to vascular imaging and assessment, and more particularly, but not exclusively, to synchronization between a three-dimensional vascular model and an imaging device during a patient-catheterized imaging procedure.

BACKGROUND

Coronary arterial stenosis is one of the most serious forms of arterial disease. In clinical practice, stenosis severity is estimated by using either simple geometrical parameters, such as determining the percent diameter of a stenosis, or by measuring hemodynamically based parameters, such as pressure-based myocardial Fractional Flow Reserve ("FFR"). FFR is a measurement regarding a functional significance of coronary stenoses. In the past, known FFR measurement techniques included the insertion of a 0.014" guidewire equipped with a miniature pressure transducer located across an arterial stenosis. Pressure in the artery would be measured at the stenosis and upstream from the stenosis. A ratio of these pressures represents the maximal blood flow in the area of stenosis and the maximal blood flow in approximately the same location without stenosis.

Currently, FFR may be determined non-invasively through computational fluid dynamic modeling of the blood flow through the arteries. Alternatively, FFR may be determined by calculating vascular resistances from vascular dimensions and identifying how the vascular resistances change when the coronary arteries are normalized. This normalization smooths vascular locations and virtually removes potential stenoses, where resistances calculated from the normalized vasculature provide an indication of maximal blood flow.

Early studies have demonstrated that FFR values less than 0.75 provide an accurate predictor of ischemia. Further, FFR values greater than 0.75 provide an indication that deferral of percutaneous coronary intervention for corresponding lesions should be safe. An FFR cut-off value of 0.8 is typically used in clinical practice to guide revascularization, supported by long-term outcome data. Typically, an FFR value in a range of 0.75-0.8 is considered a 'grey zone' having uncertain clinical significance.

To determine vascular dimensions for calculating FFR, a three-dimensional model of a patient's coronary arteries is constructed. Oftentimes, the three-dimensional model is created from two or more angiographic x-ray images that are recorded at different viewing angles with respect to the patient. The angiographic x-ray images are usually recorded by a C-arm in a catheterization laboratory.

The C-arm enables an operator to rotate around a patient's heart and acquire angiographic image(s) of different viewpoints of a patient's coronary arteries and/or lesions of interest. Generally, the C-arm is heavy to maneuver, and every image requires X-ray radiation and an injection of contrast material. Navigating a device, such as a stent, through a patient's coronary arteries is a task that requires the C-arm to track the placement of the stent along a coronary path to a target location. Currently, this tracking increases the amount of dose and dye needed for imaging because images from different angles and over different times are needed as the stent is moved through the arteries.

SUMMARY

The example methods, apparatus, and system disclosed herein are configured to synchronize a three-dimensional model of a patient's coronary arteries with a medical imaging device, such as a C-arm. Specifically, the methods, apparatus, and system disclosed herein register a model of a patient's coronary arteries with a coordinate system of a C-arm medical imaging device. After a model is created, the example system, apparatus, and methods register the model with the C-arm by referencing or assigning coordinates of the C-arm to corresponding rotational orientations of the model. The registration corresponds to a direction an image intensifier of the C-arm is facing, where the image intensifier faces one (two-dimensional) side of the three-dimensional model.

Rotation of the C-arm corresponds to changing a direction the image intensifier faces. The system, methods, and apparatus detect this rotation of the C-arm and accordingly update which side of the patient's coronary arteries, as represented by the three-dimensional model, is presently facing the image intensifier. The view from the image intensifier of the C-arm, as depicted by the orientation of the three-dimensional model, is shown within a user interface of a computer system. A clinician may move the C-arm to desired positions, for example, as a stent is being placed. The clinician may then use the corresponding view of the three-dimensional model to guide stent placement and determine when an updated image is necessary. This synchronization accordingly enables a clinician to position the C-arm to quickly obtain a clearer angle of certain vascular features to update the three-dimensional model.

The example system, methods, and apparatus also enable a user to rotate or otherwise maneuver the three-dimensional model to investigate a geometry of the patient's coronary vessel tree. In these embodiments, movement of the three-dimensional model reduces the number of x-ray images needed since two or three images may be used to construct a complete model, thereby providing views that were not imaged using the C-arm. This reduces a radiation exposure of the patient and the amount of contrast used. Moreover, the three-dimensional model, being a virtual object, can be rotated to viewpoints impossible for the C-arm to reach, enabling an operator to study the tree structure in greater detail. The system, methods, and apparatus are configured to determine how a three-dimensional model is rotated and provide corresponding instructions for the C-arm to move or rotate in a similar manner. If a clinician identifies an area of interest within the three-dimensional model that may need further imaging based on updated patient conditions, such as placement of a stent, the clinician may select an input that causes the C-arm to acquire an image at its present location. The synchronization of the C-arm reduces time from having the clinician manually position the C-arm to an approximate view that is shown of the three-dimensional model.

As disclosed herein, the example system, methods, and apparatus correlate coordinates of a three-dimensional model to a lateral angular axis (RAO angulation and LAO angulation) and a vertical angular axis (cranial angulation and caudal angulation) of a C-arm. In some embodiments, the C-arm may be moved along a track to move closer or away from a patient, which provides movement along at least one of an x-axis, a y-axis, and a z-axis. In these embodiments, the example system, methods, and apparatus additionally provide correlation of the three dimensional model to the x, y, and/or z-axes.

In light of the disclosure herein and without limiting the disclosure in any way, in a first aspect of the present disclosure, which may be combined with any other aspect listed herein unless specified otherwise, an apparatus for synchronizing a three-dimensional model of a patient's coronary arteries with an orientation of a medical imaging device includes a memory device storing a three-dimensional model of a patient's coronary arteries. The three-dimensional model includes a centerline through each of the coronary arteries. Each sample point along the respective centerline is defined in a three-dimensional coordinate system and is associated with vascular geometric information. The apparatus also includes a processor communicatively coupled to the memory device. The processor is configured to receive an instruction to register the three-dimensional model to a medical imaging device, and determine an orientation of the three-dimensional model that corresponds to a zero-degree starting position of the medical imaging device. The processor is also configured to receive potential rotational angulation positions of the medical imaging device, determine angular coordinates for the three-dimensional model that correspond to the potential rotational angulation positions of the medical imaging device, and store to the memory device a correlation between the determined angular coordinates for the three-dimensional model and the potential rotational angulation positions of the medical imaging device. The processor is further configured to determine a current view angle orientation of the medical imaging device, use the correlation between the determined angular coordinates for the three-dimensional model and the potential rotational angulation positions of the medical imaging device to rotate the three-dimensional model using the current view angle orientation of the medical imaging device, and display the rotated three-dimensional model in a user interface in a viewpoint orientation that matches the current view angle orientation of the medical imaging device.

In accordance with a second aspect of the present disclosure, which may be used in combination with any other aspect listed herein unless stated otherwise, the processor is further configured to determine the orientation of the three-dimensional model by identifying a two-dimensional face or a plane of the three-dimensional model that aligns with a view angle at the zero-degree starting position of an image intensifier of the medical imaging device.

In accordance with a third aspect of the present disclosure, which may be used in combination with any other aspect listed herein unless stated otherwise, the identified two-dimensional face or the plane of the three-dimensional model corresponds to a top-down view of the patient's coronary arteries when the patient is laying supine.

In accordance with a fourth aspect of the present disclosure, which may be used in combination with any other aspect listed herein unless stated otherwise, the vascular geometric information includes at least one of a vascular diameter, a vascular radius, a cross sectional area, a cross sectional profile, a vascular wall curvature, or vascular branching.

In accordance with a fifth aspect of the present disclosure, which may be used in combination with any other aspect listed herein unless stated otherwise, the medical imaging device includes a C-arm configured to record x-ray angiographic images.

In accordance with a sixth aspect of the present disclosure, which may be used in combination with any other aspect listed herein unless stated otherwise, the potential rotational angulation positions of the medical imaging device include RAO angulation positions, LAO angulation positions, cranial angulation positons, and caudal angulation positions.

In accordance with a seventh aspect of the present disclosure, which may be used in combination with any other aspect listed herein unless stated otherwise, the angular coordinates for the three-dimensional model include coordinates along a roll axis and a pitch axis.

In accordance with an eighth aspect of the present disclosure, which may be used in combination with any other aspect listed herein unless stated otherwise, the angular coordinates correspond to an amount the three dimensional model is rotated along the roll axis and the pitch axis.

In accordance with a ninth aspect of the present disclosure, which may be used in combination with any other aspect listed herein unless stated otherwise, the potential rotational angulation positions of the medical imaging device are at least one of stored in the memory device, received from the medical imaging device, or received via user input via an interface.

In accordance with a tenth aspect of the present disclosure, which may be used in combination with any other aspect listed herein unless stated otherwise, the processor is further configured to receive from the medical imaging device a message that is indicative of at least one of (i) a relative position change from the zero-degree starting positon of the medical imaging device provided in a rotational angulation position, or (ii) an absolute position of the medical imaging device provided in a rotational angulation position, determine a new viewpoint orientation for the three-dimensional model based on the at least one of (i) or (ii) and the correlation between the determined angular coordinates for the three-dimensional model and the potential rotational angulation positions of the medical imaging device, rotate the three-dimensional model to the new viewpoint orientation, and display in the user interface the rotated three-dimensional model.

In accordance with an eleventh aspect of the present disclosure, which may be used in combination with any other aspect listed herein unless stated otherwise, the processor is further configured to receive an imaging message indicative that a medical image is to be acquired, transmit an imaging instruction message to the medical imaging device, and receive the medical image, the medical image acquired by the medical imaging device in the new viewpoint orientation.

In accordance with a twelfth aspect of the present disclosure, which may be used in combination with any other aspect listed herein unless stated otherwise, the processor is further configured to identify coronary arteries in the medical image, determine centerlines through the identified coronary arteries, determine sample points along the centerlines in the three-dimensional coordinate system, determine vascular geometric information for the sample points along the centerline, determine a correspondence between the coronary arteries in the medical image and the three-dimensional model using at least the centerlines of the medical image and the centerlines of the three-dimensional model, and update the three-dimensional model with the determined vascular geometric information from the medical image.

In accordance with a thirteenth aspect of the present disclosure, which may be used in combination with any other aspect listed herein unless stated otherwise, the imaging instruction message includes at least one of an indication to record the medical image, a rotation instruction, a lateral movement instruction, or a zoom-magnification instruction.

In accordance with a fourteenth aspect of the present disclosure, which may be used in combination with any other aspect listed herein unless stated otherwise, the processor is configured to display the medical image in conjunction with the three-dimensional model.

In accordance with a fifteenth aspect of the present disclosure, which may be used in combination with any other aspect listed herein unless stated otherwise, the processor is configured to calculate and display, in the user interface, fractional flow reserve ("FFR") values for the three-dimensional model.

In accordance with a sixteenth aspect of the present disclosure, which may be used in combination with any other aspect listed herein unless stated otherwise, a method for synchronizing a three-dimensional model of a patient's coronary arteries with an orientation of a medical imaging device includes storing, in a memory device, a three-dimensional model of a patient's coronary arteries, the three-dimensional model including a centerline through each of the coronary arteries, each sample point along the respective centerline being defined in a three-dimensional coordinate system and being associated with vascular geometric information. The example method also includes determining, via a processor communicatively coupled to the memory device, an orientation of the three-dimensional model that corresponds to a zero-degree starting position of a medical imaging device. The method further includes receiving, in the processor, potential rotational angulation positions of the medical imaging device, determining, via the processor, angular coordinates for the three-dimensional model that correspond to the potential rotational angulation positions of the medical imaging device, and storing, to the memory device via the processor, a correlation between the determined angular coordinates for the three-dimensional model to the potential rotational angulation positions of the medical imaging device. Moreover, the method includes determining, via the processor, a current viewpoint of the three-dimensional model displayed in a user interface, and using, via the processor, the current viewpoint of the three-dimensional model and the correlation between the angular coordinates for the three-dimensional model and the potential rotational angulation positions of the medical imaging device to cause the medical image device to rotate to a corresponding view angle orientation.

In accordance with a seventeenth aspect of the present disclosure, which may be used in combination with any other aspect listed herein unless stated otherwise, the medical imaging device includes a C-arm and the method is performed in a catheterization laboratory during at least one of a stent placement, a percutaneous coronary intervention, or an FFR determination.

In accordance with an eighteenth aspect of the present disclosure, which may be used in combination with any other aspect listed herein unless stated otherwise, the method further includes receiving, in the processor, for the medical imaging device, at least two medical images recorded at different view angles with respect to the patient, the at least two medical images including depictions of the patient's coronary arteries, identifying, via the processor, the coronary arteries in the at least two medical images, determining, via the processor, centerlines through the identified coronary arteries, determining, via the processor, sample points along the centerlines in the three-dimensional coordinate system, determining, via the processor, vascular geometric information for the sample points along the centerlines, creating the three-dimensional model using the centerlines, the sample points along the centerlines in the three-dimensional coordinate system, and the vascular geometric information, and storing the three-dimensional model to the memory device.

In accordance with a nineteenth aspect of the present disclosure, which may be used in combination with any other aspect listed herein unless stated otherwise, the processor causes the medical image device to rotate by transmitting at least one instruction message to the medical image device, the at least one instruction message including at least one of (i) a relative position change from the zero-degree starting positon of the medical imaging device provided in a rotational angulation position, or (ii) an absolute position of the medical imaging device provided in a rotational angulation position.

In accordance with a twentieth aspect of the present disclosure, which may be used in combination with any other aspect listed herein unless stated otherwise, the potential rotational angulation positions of the medical imaging device include RAO angulation positions, LAO angulation positions, cranial angulation positons, and caudal angulation positions, and the angular coordinates for the three-dimensional model include coordinates along a roll axis and a pitch axis.

In a twenty-first aspect of the present disclosure, any of the structure, functionality, and alternatives disclosed in connection with any one or more of FIGS. 1 to 17 may be combined with any other structure, functionality, and alternatives disclosed in connection with any other one or more of FIGS. 1 to 17.

In light of the present disclosure and the above aspects, it is therefore an advantage of the present disclosure to provide synchronization between a three-dimensional model of a patient's coronary arteries and an orientation/position of a medical imaging device, such as a C-arm.

It is another advantage of the present disclosure to enable a clinician to update a three-dimensional model of a patient's coronary arteries in real-time during a catheterization laboratory procedure, such as placement of a stent or determining FFR values.

It is yet another advantage of the present disclosure to change an orientation and/or position of a C-arm by rotating a three-dimensional model of a patient's coronary arteries.

Additional features and advantages are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not have to have all of the advantages listed herein and it is expressly contemplated to claim individual advantageous embodiments separately. Moreover, it should be noted that the language used in the specification has been selected principally for readability and instructional purposes, and not to limit the scope of the inventive subject matter.

BRIEF DESCRIPTION OF THE DRAWINGS

Some embodiments of the invention are herein described, by way of example only, with reference to the accompanying drawings and images. With specific reference now to the drawings and images in detail, it is stressed that the particulars shown are by way of example and for purposes of illustrative discussion of embodiments of the invention. In this regard, the description taken with the drawings and images makes apparent to those skilled in the art how embodiments of the system, methods, and apparatus disclosed herein may be practiced.

DETAILED DESCRIPTION

Figure 1:
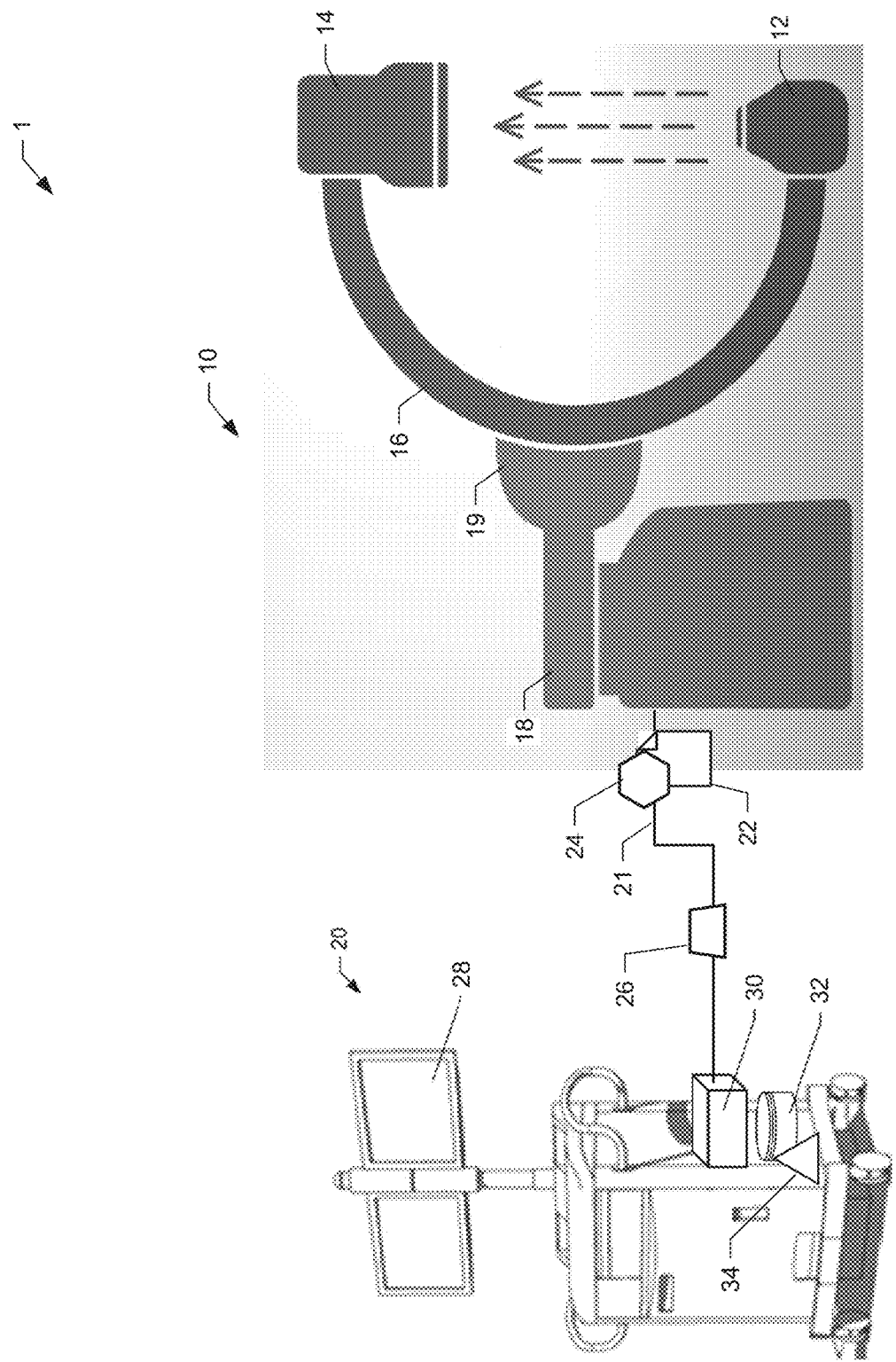
FIG. 1 is a diagram of an example vascular imaging system including a medical imaging device and a workstation, according to an example embodiment of the present disclosure.

The present disclosure relates to a system, methods, and apparatus for synchronizing a three-dimensional model with a medical imaging device. Reference is made herein to a three-dimensional model of a patient's coronary arteries. However, it should be appreciated that the system, methods, and apparatus disclosed herein may provide for synchronization between three-dimensional models of other vascular networks.

The example system, methods, and apparatus determine or otherwise create a correlation between angular coordinates of a three-dimensional model and potential rotational angular positions of a medical imaging device. The correlation is used to ensure that a three-dimensional model, as shown in a display interface, is shown in the same viewpoint as, for example, an image intensifier of the medical imaging device (e.g., a C-arm). Movement of the C-arm is detected by the system, methods, and apparatus, which update the viewpoint of the three-dimensional model. Likewise, rotation of the three-dimensional model is detected by the system, methods, and apparatus, which cause the medical imaging device to rotate in a corresponding manner.

In some embodiments, the rotational angular positions of a medical imaging device include RAO angulation positions and LAO angulation positions, which are provided along a lateral (side-to-side) rotational axis with respect to a patient. Additionally or alternately, the rotational angular positions include cranial angulation positons and caudal angulation positions, which are provided along a vertical (head-to-toe) rotational axis with respect to a patient. It should be appreciated that other rotational or linear positions of a medical imaging device may also be used, such as movement along x, y, or z axes.

As disclosed herein, a three-dimensional model may be rotated by an amount specified by angular coordinates. The angular coordinates may include a roll axis and a pitch axis. The roll axis may correspond to RAO and LAO angular positions of the medical imaging device, while the pitch axis may correspond to cranial and caudal angulation positions. Coordinates along the roll axis and pitch axis specify how the three-dimensional model is to be virtually rotated to a desired viewpoint for display on a user interface. The viewpoint may correspond to a two-dimensional projected view of the three-dimensional model, which is synchronized to the two-dimensional view angle orientation of the medical imaging device, as described herein.

In some embodiments, the three-dimensional model may also be rotated along a pitch axis. If a medical imaging device is not able to move along a corresponding rotational angular position, the example methods, apparatus, or system may display an alert indicative that the movement of the three-dimensional model is outside the movement capability of the medical imaging device. Such an alert indication may also be provided if the three-dimensional model is moved along a roll and/or pitch axis to a degree that exceeds a travel limit of the medical imaging device. In some embodiments, the system, methods, and apparatus disclosed herein may lock the three-dimensional model to travel ranges of a medical imaging device to prevent a clinician from exceeding a travel limit.

The example synchronization provided by the system, methods, and apparatus disclosed herein reduces an amount of contrast agent or radiation dosage received by a patient during treatment in a catheterization laboratory. For example, after acquiring enough two-dimensional images, the methods, apparatus, and system disclosed herein create a three-dimensional model. While the patient is still catheterized, a clinician may review the three-dimensional model to identify any areas that appear unclear or have potential modeling errors. For example, some vessels may be designated in the model as being connected where in fact the vessels cross at different heights. In other instances, vessel curvature in a model may not be smooth, instead being shown as abrupt changes in direction or width. Such artifacts may be due to extrapolation errors from having too few two-dimensional images. In these instances, the clinician positions the three-dimensional model such that an area of concern is shown in a current viewpoint. The example methods, apparatus, and system determine corresponding angular positions of the medical imaging device, and transmit instructions to the medical imaging device to rotate to the identified position/orientation. The example methods, apparatus, and system then cause the medical imaging device to acquire at least one additional two-dimensional image, which is then used to update the three-dimensional model. Once the clinician is satisfied that the three-dimensional model is accurate, the example methods, apparatus, and system determine an index indicative of vascular function, such as FFR values. The computational efficiency and quick imaging provided by synchronization to the three-dimensional model enable all of the above operations to be carried out while the patient is still catheterized.

In another example, the methods, apparatus, and system provide synchronization during stent placement or any other catheterization laboratory procedure to inflate diseased locations of a patient's coronary arteries. In these examples, a clinician may track stent placement using the three-dimensional model. As the model is being rotated, the example methods, system, and apparatus cause a medical imaging device to rotate in a corresponding manner. If an updated view is needed, the clinician provides an instruction, which causes the example methods, system, and apparatus to record an image using the medical imaging device. The image may be displayed in conjunction with the model and/or may be used to update the model. This configuration enables a clinician to obtain additional two-dimensional angiographic images only as needed during treatment, where the medical imaging device is already in position to acquire an image when a clinician determines that an image is needed.

The example methods, apparatus, and system also detect movement or rotation of a medical imaging device. In response to the detected movement or rotation, the methods, apparatus, and system update an orientation of a displayed three-dimensional model of a patient's coronary arteries. Rotation of the three-dimensional model based on manual movement of the medical imaging device shows a clinician a viewpoint of a patient's coronary arteries that are facing the imaging device. Such a configuration may enable a clinician to determine a desired orientation for the model using external locations (provided by the medical imaging device) relative to a patient.

Example Vascular Imaging System

FIG. 1 is a diagram of an example vascular imaging system 1 including a medical imaging device 10 and a workstation 20, according to an example embodiment of the present disclosure. The medical imaging device 10 includes, for example, a C-arm. The example medical imaging device 10 in the illustrated example includes a radiation source 12 and an image intensifier 14. The example radiation source 12 is configured to emit ionizing radiation, which travels through a patient. For analysis of a patient's coronary arteries, the radiation source 12 is directed towards a patient's heart. The image intensifier 14 detects the radiation after the radiation has passed through a patient and records two-dimensional images that are indicative of the detected radiation intensity and/or ionization as the radiation contact's the patient's tissues. The image intensifier 14 is located directly across from the radiation source 12.

The radiation source 12 and the image intensifier 14 are positioned directly across from each other via a coupling to a support structure 16. As shown in FIG. 1, the support structure 16 may have a c-shape, with the image intensifier 14 and radiation source 12 being connected to opposing ends of the 'c'. The support structure 16 is mechanically coupled to a base 18, which is connected to a floor or ceiling. The base 18 includes a pivot section 19, which is configured to rotate the support structure 16 in one or more angular axes. The example pivot section 19 includes motors that cause the support structure to rotate and/or otherwise move along a track to provide rotation of the image intensifier 14 and the radiation source 12.

Figure 2:
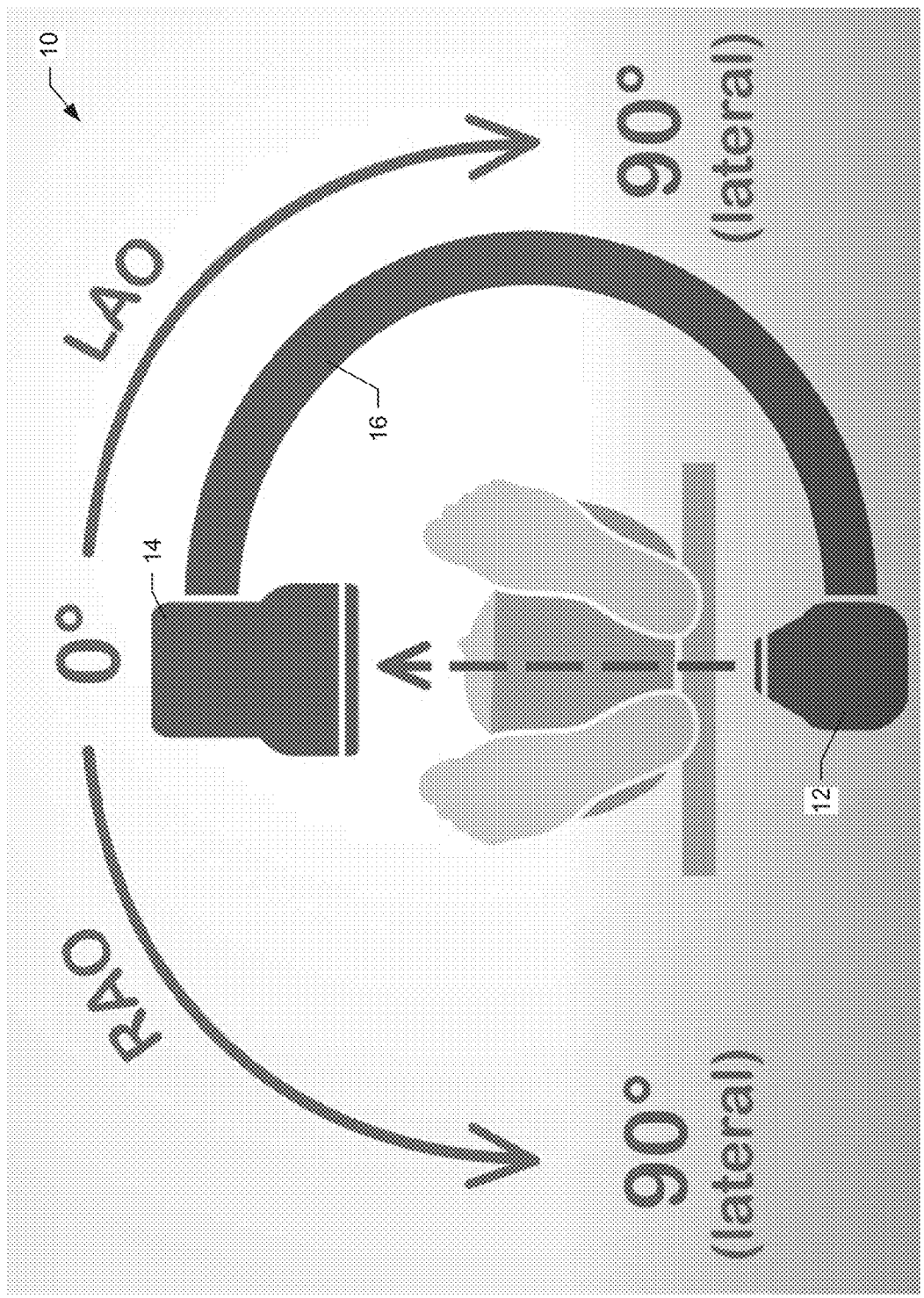
FIG. 2 shows a first angular axis along which a support structure of the medical imaging device of FIG. 1 may be rotated, according to an example embodiment of the present disclosure.

FIG. 2 shows a first angular axis along which the support structure 16 may be rotated, according to an example embodiment of the present disclosure. The first angular axis may be referred to herein as a lateral (side-to-side) angular or rotational axis. As shown in FIG. 2, the axis includes a zero-degree starting position. Clockwise rotation is referred to herein as LAO angulation, and counter-clockwise rotation is referred to herein as RAO angulation. In some embodiments, the support structure 16 may be rotated 90° along the RAO and LAO directions. In other embodiments, the support structure 16 may be rotated greater than 90° or less than 90°.

Figure 3:
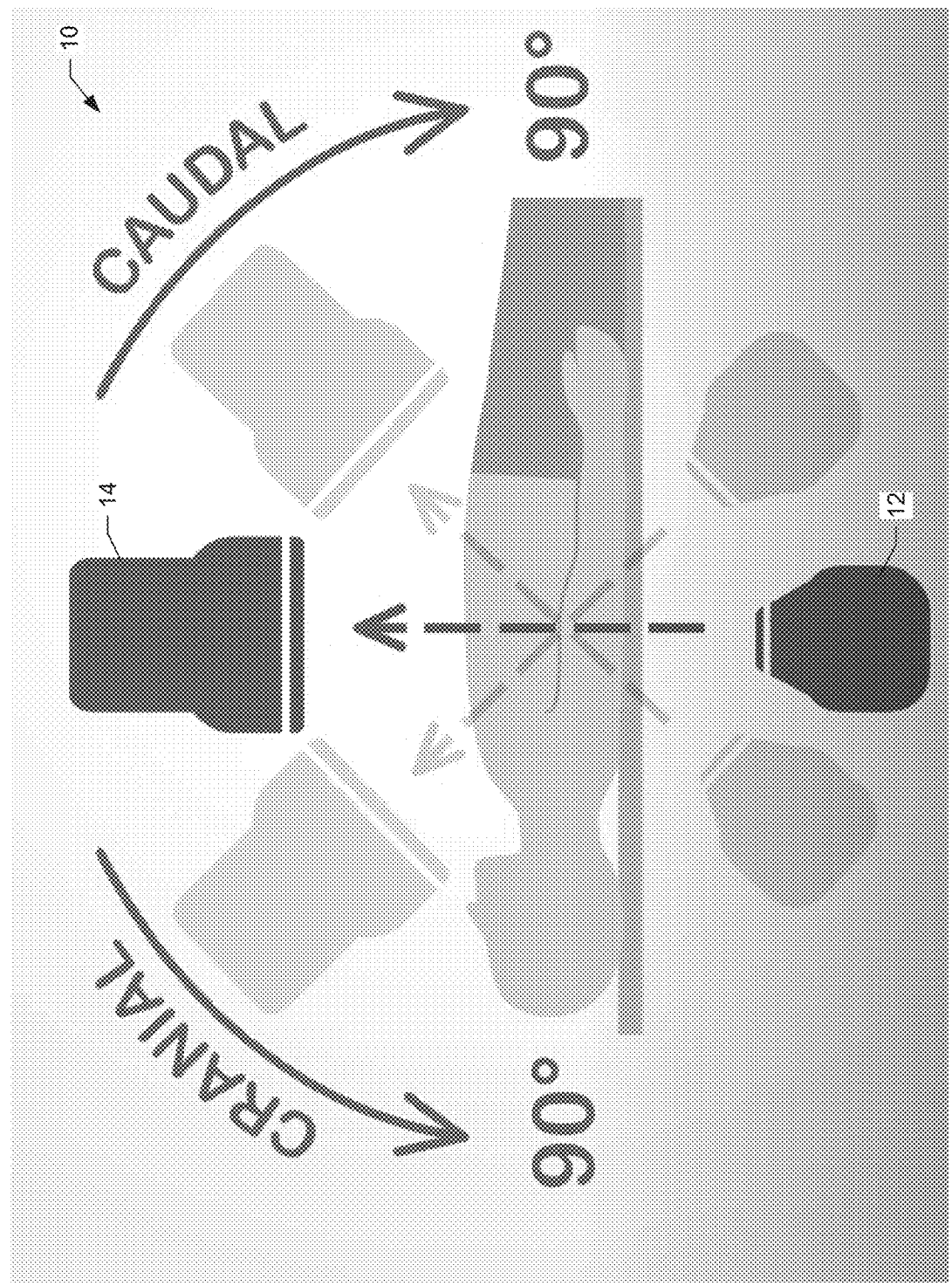
FIG. 3 shows a second angular axis along which the support structure of the medical imaging device of FIG. 1 may be rotated, according to an example embodiment of the present disclosure.

FIG. 3 shows a second angular axis along which the support structure 16 may be rotated, according to an example embodiment of the present disclosure. The second angular axis may be referred to herein as a vertical (head-to-toe) angular or rotational axis. As shown in FIG. 3, the axis includes a zero-degree starting position. Clockwise rotation is referred to herein as caudal angulation, and counter-clockwise rotation is referred to herein as cranial angulation. In some embodiments, the support structure 16 may be rotated 90° along the caudal and cranial directions. In other embodiments, the support structure 16 may be rotated greater than 90° or less than 90°.

FIGS. 2 and 3 show that for each rotation along the first and second angular axes, the radiation source 12 is pointed toward the patient's heart. Likewise, the image intensifier 14 is also pointed towards the patient's heart. Rotation of the support structure 16 enables the patient's heart to be imaged from different viewpoints. In some embodiments, the support structure 16 may also be moved along x, y, and/or z axes with respect to the patient.

Returning to FIG. 1, the medical imaging device 10 is communicatively coupled to the workstation 20 via a link 21, which may include any wireless or wired link. The link 21 may include a network, such as a Wi-Fi network, an Ethernet network, a local area network, or a wide area network, such as the Internet. The link 21 enables the medical imaging device 10 to transmit acquired images 22 recorded by the image intensifier 14 to the workstation 20.

The link 21 also enables the medical imaging device 10 to transmit position information, such as rotational coordinates 24 of the support structure 16 or image intensifier 14.

Additionally or alternatively, the link 21 enables the workstation 20 to transmit command messages or instructions 26 to the medical imaging device 10. The command messages or instructions 26 may include an instruction to record an image. The commend messages or instructions 26 may also include an instruction to rotate the support structure 16 to a specified orientation. As described herein, the instructors 26 may include relative position data that specifies a relative position change from a zero-degree starting positon (or current position) of the support structure 16 of the medical imaging device 10. The instructions 26 may alternatively include an absolute position along the lateral and vertical rotational axes. The instructions 26 may be specified in rotational angular positions, degrees, and/or coordinates.

The example workstation 20 includes a monitor or display screen 28, a processor 30, and a memory device 32. In some embodiments, the display screen 28 may include touch-screen sensors to enable clinicians to enter inputs. The example display screen 28 is configured to display one or more user interfaces transmitted by the processor 30. The user interfaces may display the images 22 recorded by the medical imaging device 10. The user interfaces may also display a three-dimensional model of a patient's coronary arteries. The user interfaces may include one or more controls to enable a clinician to manipulate the three-dimensional model. For instance, a user interface may enable a user to rotate a three-dimensional model along a pitch and/or roll angular axis. Further, a user interface may enable a user to rotate a three-dimensional model of a patient's coronary arteries along a yaw angular axis. In some embodiments, a user interface may enable a clinician to input an instruction to cause the medical imaging device 10 to record one or more images. Further, a user interface may include a control, which when selected, causes a three-dimensional model to lock or otherwise synchronize to the medical imaging device 10, as described herein.

The example processor 30 is communicatively coupled to the display screen 28 and the memory device 32. The example processor 30 may include a controller, a microcontroller, a control unit, a server, an application specific integrated circuit ("ASIC"), a field-programmable gate array ("FPGA"), microprocessor, etc. The example processor 30 is configured to perform the operations described herein. Aspects of the present disclosure are described below with reference to flowchart illustrations and/or block diagrams of methods, apparatus (systems), and computer program products according to certain embodiments. It should be understood that the operations described herein may be defined by computer program instructions. These computer program instructions may be provided to the processor 30, such that the instructions, when executed via the processor 30 perform the operations described herein. The instructions may comprise a software application, an algorithm, and/or a routine.

The computer program instructions may be stored in the memory device 32. The example memory device 32 may include an electronic memory, a magnetic memory, an optical memory, an electromagnetic memory, an infrared memory, and/or a semiconductor memory. For example, the memory device 32 may include a portable computer diskette, a hard disk, a random access memory ("RAM"), a read-only memory ("ROM"), an erasable programmable read-only memory ("EPROM" or Flash memory), an optical fiber, a portable compact disc read-only memory ("CD-ROM"), an optical storage device, a magnetic storage device, or any suitable combination of the foregoing.

The example processor 30 in cooperation with the memory device 32 is configured to create a three-dimensional model of a patient's coronary arteries using, for example, at least two images 22 from the medical imaging device 10. The images 22 may be recorded at different angles with respect to the patient's coronary arteries. As described below in more detail, the processor 30 identifies vessel centerlines and/or boundaries in the images. The processor 30 uses homologies or similarities between features of the vessel to correlate the same vessel location shown in the different images. The processor 30 may then determine sample points along the centerlines. Further, the processor 30 determines vascular geometric information for the sample points along the centerlines. Using the homologies and/or similarities, the processor 30 combines the same centerlines shown in the different images. The processor 30 also combines the vascular geometric information for the same location (as determined in the different images) to determine a three-dimensional geometry. The vascular geometric information and/or the three-dimensional geometry may include at least one of a vascular diameter, a vascular radius, a cross sectional area, a cross sectional profile, a vascular wall curvature, or vascular branching. As described herein, combining may include determining which vascular geometric information for a particular location is most likely representative of the vessel geometry using, for example, a projection degree from which a corresponding image was recorded by the medical imaging device 10, image information indicative that a substantially side-view of a vessel is shown rather than a front or rear view, and/or information indicative that visual interference or obstruction is not present. The visual interference may result from a crossing vessel or other tissue. After the three-dimensional geometries are determined, vessel wall boundaries are formed with respect to the combined centerlines, thereby forming a three-dimensional model. The processor 30 may also apply a three-dimensional coordinate system to the three-dimensional model, where each point along a centerline is assigned a coordinate. In some instances, the coordinate assignment may occur after the centerlines are identified in the images, which enables the processor 30 to assign similar locations in different images to the same coordinate, which is beneficial for identifying homologies and combining vascular data from multiple images together. FIG. 1 shows that the memory device 32 is configured to store a three-dimensional model 34 of a patient's coronary arteries.

In addition to creating three-dimensional models from two-dimensional images, the example processor 30 in cooperation with the memory device 32 is configured to determine values indicative of vascular health. As described below in more detail, the example processor 30 is configured to determine vascular resistances using the three-dimensional model. The vascular resistances are used to approximate blood flows and/or pressures within, for example, a patient's coronary arteries. Further, the processor 30 may normalize or otherwise smooth the three-dimensional model. This normalization reduces abrupt narrowing of the coronary arteries that may be attributed to a lesion or stenosis. The processor 30 determines vascular resistances in the normalized model, which may be indicative of vascular bed resistances. The processor 30 may further determine blood flows and/or pressures in the normalized model. The processor 30 calculates a ratio of the blood flows, pressures, and/or resistances for the same location throughout the three-dimensional model pre and post normalization. The calculated ratios correspond to FFR values.

The example processor 30 is also configured to provide for synchronization between the medical imaging device 10 and one or more three-dimensional models 34. The synchronization may be provided to improve a quality of a three-dimensional model where a first set of medical images may not have captured certain vascular features correctly. The synchronization may also be used during a medical treatment, such as stent placement, where updated medical images are needed to access or track placement of the stent.

To provide synchronization, the example processor 30 is configured to create a correlation between a three-dimensional model and the medical imaging device 10. The correlation may be stored in a file or other data structure within the memory device 32. The correlation relates coordinates or rotational angular degrees of a three-dimensional model to the lateral and vertical angular axes of the medical imaging device 10.

Figures 4, 5:
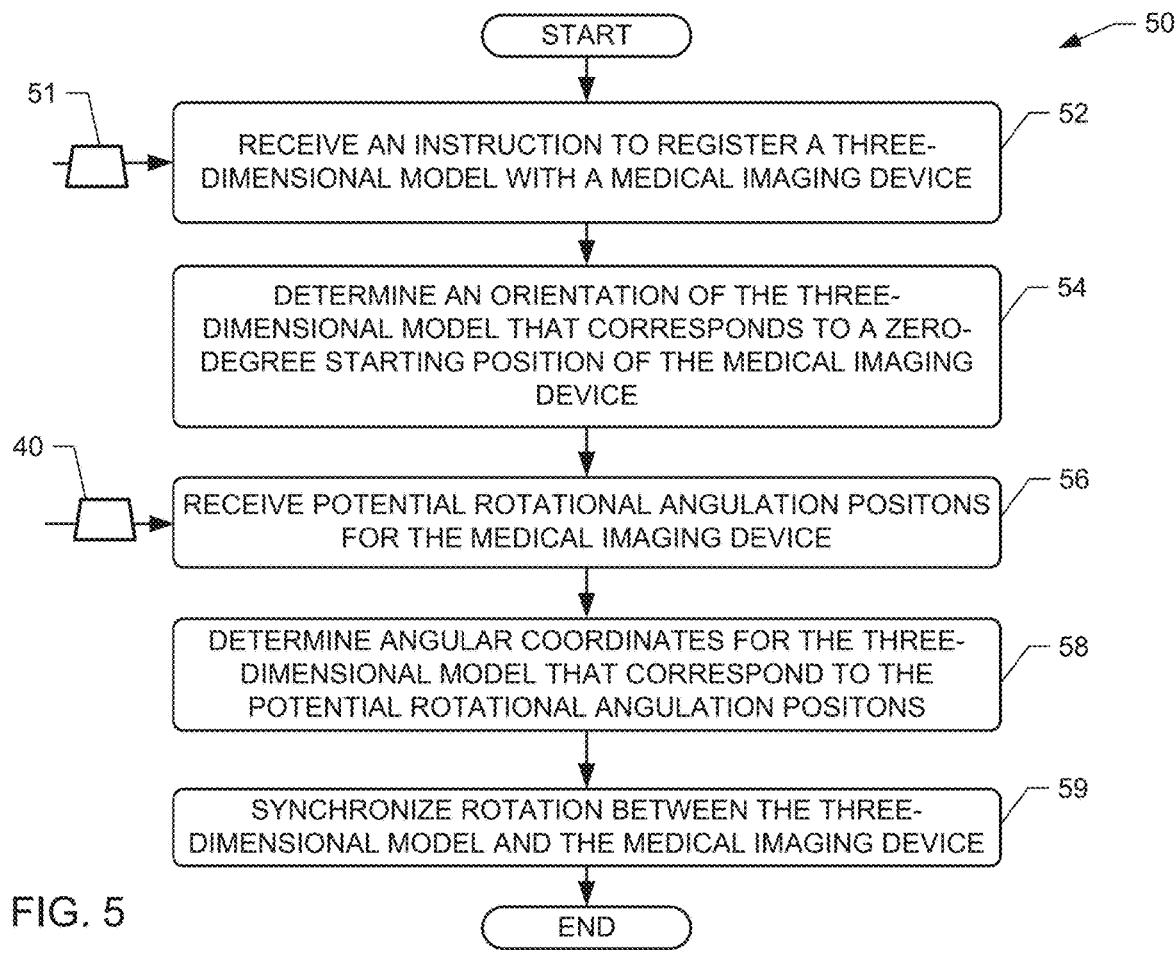
FIG. 4 is a diagram of an example correlation file to synchronize a three-dimensional model of a patient's coronary arteries with a medical imaging device, according to an example embodiment of the present disclosure.
FIG. 5 is a flow diagram of an example procedure that uses the correlation file of FIG. 4 to synchronize a three-dimensional model of a patient's coronary arteries with a medical imaging device, according to an example embodiment of the present disclosure.

FIG. 4 is a diagram of an example correlation file 40 used by the processor 30 to synchronize a three-dimensional model of a patient's coronary arteries with the medical imaging device 10, according to an example embodiment of the present disclosure. In this embodiment, RAO angulation of the medical imaging device 10 corresponds to positive roll of a three-dimensional model while LAO angulation of the medical imaging device 10 corresponds to negative roll of the three-dimensional model. Further, cranial angulation of the medical imaging device 10 corresponds to negative pitch of the three-dimensional model and caudal angulation of the medical imaging device 10 corresponds to positive pitch of the three-dimensional model. Further, a zero-point starting position of the medical imaging device 10 (e.g., RAO 0°, LAO 0°, cranial 0°, and caudal 0°), corresponds to a viewpoint of a three-dimensional model of a front face or plane when a patient is in a supine position. In other words, the viewpoint of the three-dimensional model for an origin point of the roll and pitch angular axes corresponds to a plane that is facing the image intensifier 14 when the medical imaging device is placed at the zero-point starting position.

The correlation file 40 shown in FIG. 4 relates a degree of angulation to a degree of roll or pitch of the three-dimensional model. In some instances, there is a one-to-one correspondence. In other instances, the relationship in degrees may be non-linear. In an example, the processor 30 may receive rotational coordinates 24 from the medical imaging device 10 indicative of rotation of the support structure 16. Specifically, the rotational coordinates 24 may specify cranial 10° and ROA 10°. The processor 30 uses the correlation file 40 to determine that a selected three-dimensional model displayed in a user interface on the display screen 28 is to be rotated −11° along a pitch axis and 12° along the roll axis. In a similar manner, the processor 30 may receive roll/pitch degrees based on a clinician rotating a three-dimensional model. In response, the processor 30 determines the lateral and vertical angulation degrees for the medical imaging device 10. The processor 30 then transmits instructions 26 to the medical imaging device 10 indicative of the determined lateral and vertical angulation degrees.

It should be appreciated that the degrees may be absolute or relative. For example, the medical imaging device 10 may transmit an absolute position of the support structure 10. For absolute degrees, the processor 30 uses the correlated degrees as a corresponding absolute position for the three-dimensional model. Alternatively, the medical imaging device 10 may transmit relative rotation of the support structure 16. For relative degrees, the processor 30 rotates the three-dimensional model from a current position based on the determined relative roll and pitch degree changes.

In some embodiments, the correlation file 40 of FIG. 4 may be replaced by a transfer function. In these instances, there is a lineal, proportional, quadratic, etc. relationship between the roll/pitch of a three-dimensional model and the angulation of the medical imaging device 10. Further, it should be appreciated that the memory device 32 may store a separate transfer function and/or correlation file 40 for each different type of medical imaging device 10.

The example correlation file 40 and/or transfer function may be determined based on known relationships between angulation of the medical imaging device 10 and a three-dimensional model. In other examples, the processor 30 may perform an iterative method where a three-dimensional model is rotated by +/− one degree along the roll and pitches axes, and the medical imaging device 10 is rotated until an acquired image matches the viewpoint of the three-dimensional model. The processor 30 may determine centerlines of vessels in an acquired image and determine if they align with vessels in the three-dimensional model as viewed in a current viewpoint. In these examples, the processor 30 determines correlations through all paths of potential travel of the support structure 16 for of the medical imaging device 10.

In yet other examples, the processor 30 may receive or acquire a template three-dimensional model from the memory device 32. The three-dimensional model may correspond to a template three-dimensional object that is placed for imaging by the medical imaging device 10. The model may include fiducials or other markers at predefined locations. The three-dimensional object may include fiducials or other markers that are placed at known distances from each other. The processor 30 causes the medical imaging device 10 to acquire an image when the model is at a defined orientation. The processor 30 may compare the fiducials shown in the image with the fiducials in the model to determine if alignment is synchronized. If not, the processor 30 may compute deltas between the fiducials to determine how the support structure 16 is to be rotated. The processor 30 then causes the support structure 16 to rotated, and causes the medical imaging device 10 to acquire another image to confirm synchronization. Such calibration may be performed prior to treatment on a patient and/or when the processor 30 is provisioned for operation with the medical imaging device 10.

In some embodiments, the correlation file 40 may also include rotational limits of the medical imaging device 10. The rotational limits correspond to an end of a track of the support structure 16 with respect to the pivot section 19. These limits may also correspond to known or estimated locations of a patient, such as their head or legs. In the illustrated example of FIGS. 2 and 3, the rotational limits may correspond to 90° RAO, LAO, cranial, and/or caudal.

FIG. 5 is a flow diagram of an example procedure 50 that uses the correlation file 40 of FIG. 4 to synchronize a three-dimensional model of a patient's coronary arteries with the medical imaging device 10, according to an example embodiment of the present disclosure. Although the procedure 50 is described with reference to the flow diagram illustrated in FIG. 5, it should be appreciated that many other methods of performing the steps associated with the procedure 50 may be used. For example, the order of many of the blocks may be changed, certain blocks may be combined with other blocks, and many of the blocks described may be optional. In an embodiment, the number of blocks may be changed based on how the correlation is determined. The actions described in the procedure 50 are specified by one or more instructions that are stored in the memory device 32, and may be performed among multiple devices including, for example the processor 30 and/or the medical imaging device 10.

The example procedure 50 begins by receiving an instruction 51 from a clinician via a user interface or control device to register a three-dimensional model with a medical imaging device (block 52). The instruction 51 may include an identification of the three-dimensional model and/or the medical imaging device 10. In other examples, the processor 30 may identify which three-dimensional model is opened in a user interface, and a device model and/or type of communicatively coupled medical imaging device 10. The instruction 51 may be received for a specific three-dimensional model of a patient's coronary arteries that are constructed using two-dimensional angiographic images previously recorded by the medical imaging device 10.

The procedure 50 continues by the processor 30 determining an orientation of the selected three-dimensional model that corresponds to a zero-degree starting position of the medical imaging device 10 (block 54). The orientation may be determined by identifying a front of the three-dimensional model based on a known orientation of coronary arteries. The orientation may also be known based on an image that was recorded by the medical imaging device 10 (in a zero-point starting position) during creation of the three-dimensional model 10 and confirming the image aligns with the model. To provide a confirmation, the processor 30 may compare centerlines in the image to the centerlines of the three-dimensional model. If the difference between the centerlines is less than a threshold, the processor 30 confirms the three-dimensional model is aligned to the zero-point starting position of the medical imaging device 10.

Next, the processor 30 determines or receives potential rotational angulation positions for the medical imaging device 10 (block 56). The potential rotational angulation positions for the medical imaging device 10 are specified in the correlation file 40. In other embodiments, the potential rotational angulation positions for the medical imaging device 10 may be expressed within a transfer function. In some instances, the potential rotational angulation positions for the medical imaging device 10 may be input by a clinician or other operator.

The example processor 30 then determines or identifies angular coordinates for the three-dimensional model that correspond to the potential rotational angulation positions for the medical imaging device 10 (block 58). The angular coordinates for the three-dimensional model that correspond to the potential rotational angulation positions may also be specified in the correlation file 40 and/or expressed within a transfer function. In some instances, the angular coordinates for the three-dimensional model may be input by a clinician and manually correlated to the potential rotational angulation positions for the medical imaging device 10.

At this point, the three-dimensional model and the medical imaging device 10 are orientated in a zero-point starting position and the processor 30 has rotational correlations between the model and the imaging device. The processor 30 is now enabled to synchronize rotation or movement between the three-dimensional model and the medical imaging device 10, as discussed below.

When the three-dimensional model is synchronized with the medical imaging device 10, the processor 30 may cause an alert or other message to be displayed when a clinician rotates the three-dimensional model to a position or orientation that is outside the range of rotation of the support section 16. In some instances (e.g., if a lock feature is enabled via a user interface), the processor 30 may prevent the three-dimensional model from being rotated past the rotational limits of the medical imaging device 10.

Returning to FIG. 1, the example workstation 20 may additionally include a mouse, touchscreen, joystick, etc. that is communicatively coupled to the processor 30 to provide input commends, such as to rotate the three-dimensional model. The mouse, touchscreen, joystick, etc. may further be used to control rotation of the medical imaging device 10. In some embodiments, a smartphone or tablet computer may be communicatively coupled to the processor 30. In these embodiments, the smartphone or tablet may include an application that displays a control interface for rotating the three-dimensional model and/or rotating the medical imaging device 10.

Example Synchronization Embodiments

Figure 6:
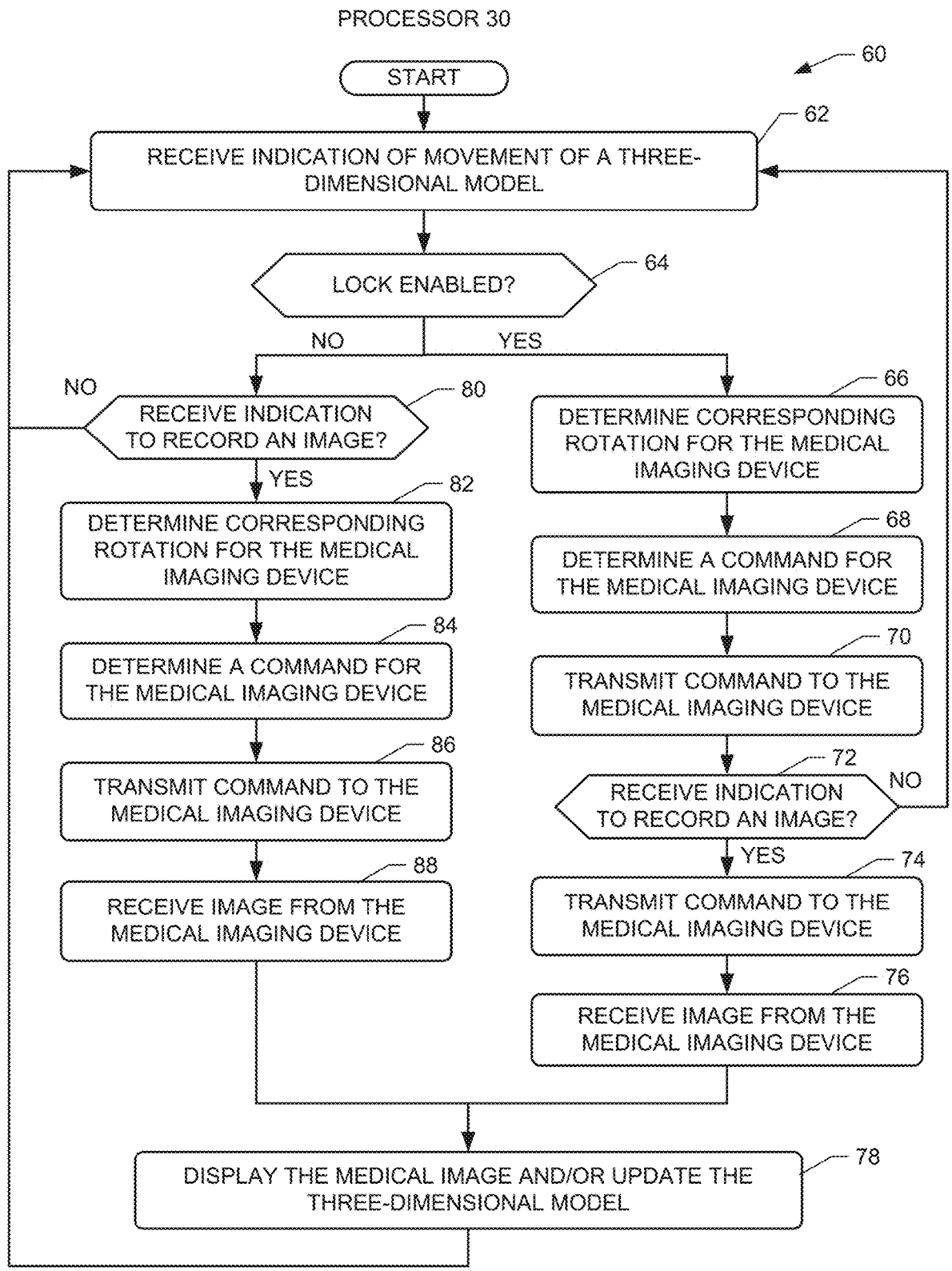
FIG. 6 is a flow diagram of an example procedure for causing a medical imaging device to rotate based on detected rotation of a three-dimensional model, according to an example embodiment of the present disclosure.

FIG. 6 is a flow diagram of an example procedure 60 for causing the medical imaging device 10 to rotate based on detected rotation of a three-dimensional model, according to an example embodiment of the present disclosure. Although the procedure 60 is described with reference to the flow diagram illustrated in FIG. 6, it should be appreciated that many other methods of performing the steps associated with the procedure 60 may be used. For example, the order of many of the blocks may be changed, certain blocks may be combined with other blocks, and many of the blocks described may be optional. In an embodiment, the number of blocks may be changed based on how the synchronization is configured. The actions described in the procedure 60 are specified by one or more instructions that are stored in the memory device 32, and may be performed among multiple devices including, for example the processor 30 and/or the medical imaging device 10.

The example procedure 60 begins when the processor 30 of FIG. 1 receives an indication of a movement of a three-dimensional model (block 62). The indication is received after the processor 30 has synchronized the three-dimensional model with the medical imaging device 10, as discussed above in connection with FIG. 5. In some embodiments, the indication may be received from a user interface that is displaying the three-dimensional model (such as model 34) on a display screen 28. The indication may be received via user interface controls or from a physical device, such as a mouse. The indication includes, for example, a number of degrees along a pitch axis and/or a roll axis the three-dimensional model was rotated with respect to a starting-point or origin.

The example processor 30 next determines if a lock feature is enabled (block 64). The lock feature may be displayed in a user interface with the three-dimensional model, and when selected, causes real-time rotation of the model to be synchronized with the medical imaging device 10. If the lock feature is enabled, the processor 30 uses the correlation file 40 (or transfer function) to determine corresponding rotation for the medical imaging device 10 based on the degrees of roll/pitch rotation of the three-dimensional model (block 66). The processor 30 determines, for example, rotational angulation positions for the support structure 16 of the medical imaging device 10 (e.g., a RAO angulation, a LAO angulation, a cranial angulation, and/or a caudal angulation).

The processor 30 then determines machine instructions or a command for the determined rotational angulation positions (block 68). The command includes a digital message or an analog signal that is indicative of the determined rotational angulation positions. For instance the command may specify a number of degrees certain motors are to rotate. In other embodiments, the command may include just the determined rotational angulation positions. The processor 30 transmits the command to the medical imaging device 10 (block 70), causing the device to rotate as instructed.

Figure 7:
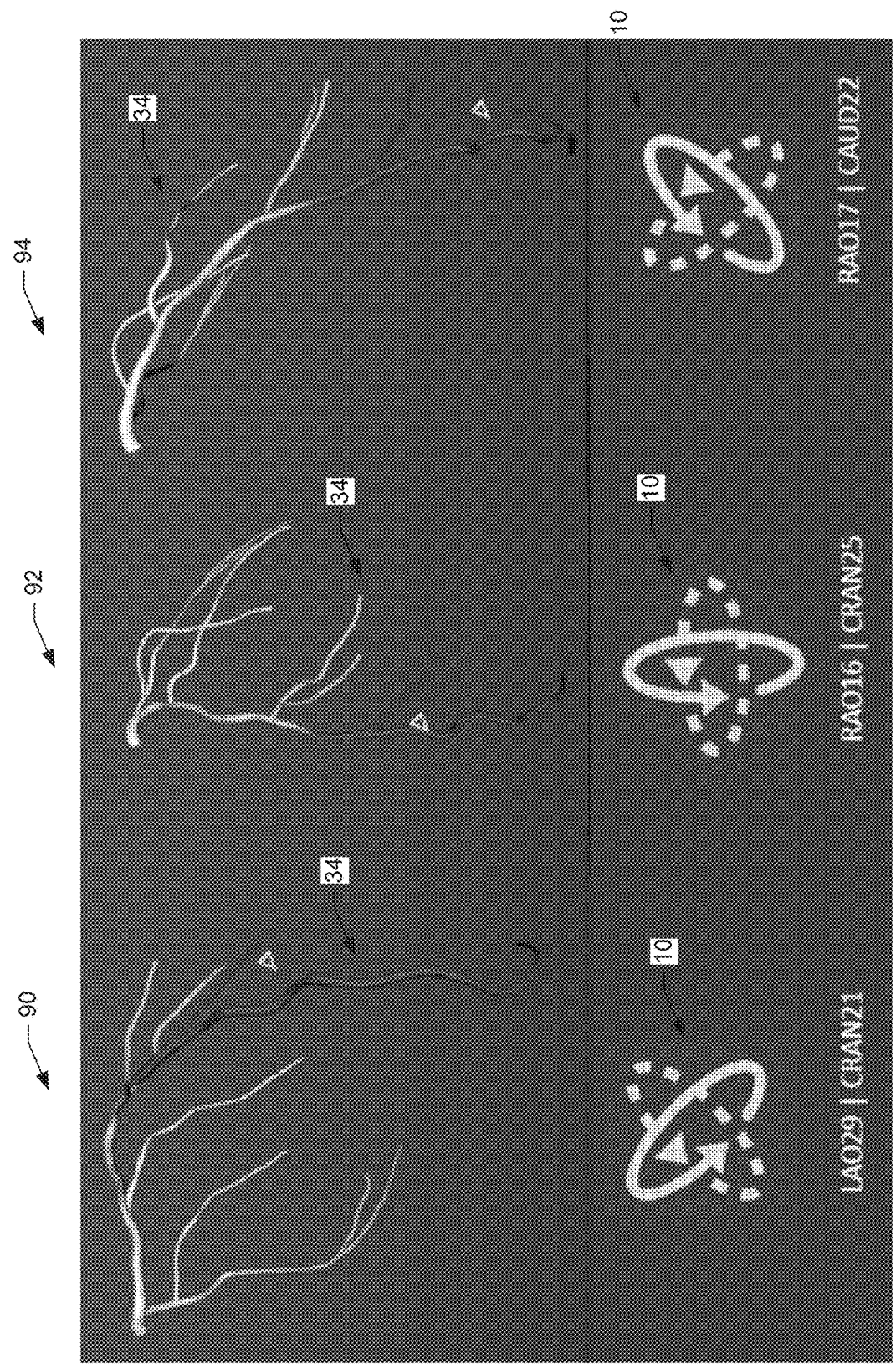
FIG. 7 is a diagram that is illustrative of a synchronization between a three dimensional model and the medical imaging device, according to an example embodiment of the present disclosure.

FIG. 7 is a diagram that is illustrative of a synchronization between a three dimensional model 34 and the medical imaging device 10, according to an example embodiment of the present disclosure. The synchronization may be provided by the processor 30 using the procedure 60 described above. In a first instance, a clinician rotates the three-dimensional model 34 to a first orientation 90. The processor 30 detects this rotation and determines a corresponding rotational angulation position for the medical imaging device 10 (LAO 29°, Cranial 21°). The processor 30 then transmits instructions causing the medical imaging device 10 to rotate accordingly. The commands or instructions cause the medical imaging device 10 to move such that the image intensifier 14 faces or otherwise projects to a region of the patient's coronary arteries that corresponds to the orientation 90 of the three-dimensional model 34 shown in the user interface.

The example processor 30 enables the clinician to rotate or otherwise maneuver the three dimensional model 34 to investigate a geometry of the vessel tree. Movement of the three dimensional model 34 reduces the number of x-ray images needed since two or three images could be used to construct a complete model, providing views that were not imaged using the medical imaging device. This reduces a radiation exposure of the patient and the amount of contrast used. Moreover, the three dimensional model 34, being a virtual object, can be rotated to viewpoints that are not possible for the medical imaging device to reach, enabling a clinician to investigate the vascular tree structure in greater detail.

In a second instance, a clinician rotates the three-dimensional model 34 to a second orientation 92. In response, the processor 30 causes the medical imaging device 10 to rotate in a synchronized manner (RAO 16°, Cranial 25°). In a third instance, a clinician rotates the three-dimensional model 34 to a third orientation 94. In response, the processor 30 causes the medical imaging device 10 to rotate in a synchronized manner (RAO 17°, Caudal 22°).

Returning to FIG. 6, the example procedure 60 continues when the processor 30 determines if an indication to record an image is received from a user interface or control device (block 72). If an indication has not been received, the procedure 60 returns to block 62 for detecting further rotation of the three-dimensional model. However, if an indication to record an image has been received, the processor 30 transmits an instruction or a command message to the medical imaging device 10 to record an image (block 74). The processor 30 then receives the medical image after it is acquired (block 76). The processor 30 may then display the medical image in a user interface in conjunction with the three-dimensional model and/or update the three-dimensional model using the new image (block 78). In some instances, the processor 30 may update the model and calculate new FFR values, which may be used to determine whether a treatment, such as placement of a stent, has been successfully preformed to remove or mitigate a vessel lesion or stenosis. The example procedure 60 then returns to block 62 for detection of further rotation of the three-dimensional model. The example procedure 60 accordingly enables a real-time synchronization of an actual viewpoint of a model with a current position of a medical imaging device.

The synchronization feature also enables a clinician to obtain a desired viewpoint more accurately for the imaging device based on a desired viewpoint of the model, which avoids irradiating and injecting dye when not necessary if the information within the model is sufficient for the clinician. Unlike an imported CT model, the example three-dimensional model can also be updated on the fly with every new navigation image acquired. Whenever contrast material is injected during the acquisition of the navigation verification images, the actual diameter data present in those images may be used by a clinician to update the model to maintain a live updated road map of the coronary arteries.

Returning to block 64 of the procedure 60, if the lock feature is not enabled, movement of the three-dimensional model does not cause real-time movement of the medical imaging device 10. Instead, the processor 30 determines if an indication to record an image has been received (block 80). If an indication has been received, the processor 30 proceeds to cause the medical imaging device 10 to rotate for synchronization with the model. This includes using the correlation file 40 (or transfer function) to determine corresponding rotation for the medical imaging device 10 based on the degrees of roll/pitch rotation of the three-dimensional model (block 82). The processor 30 then determines machine instructions or a command for the determined rotational angulation positions (block 84). The processor 30 transmits the command to the medical imaging device 10 (block 86), causing the device to rotate as instructed. The processor 30 then receives the medical image after it is acquired (block 88). The processor 30 may then display the medical image in a user interface in conjunction with the three-dimensional model and/or update the three-dimensional model using the new image (block 78). In some instances, the processor 30 may update the model and calculate new FFR values, which may be used to determine whether a treatment, such as placement of a stent, has been successfully preformed to remove or mitigate a vessel lesion or stenosis. The example procedure 60 then returns to block 62 for detection of further rotation of the three-dimensional model.

In some embodiments, the processor 30 is configured to register new images, acquired during device navigation, with the three-dimensional model. The example processor 30 uses the known viewpoint (angulation) of the medical imaging device 10 when the image is acquired to associate the image with the corresponding location on the three-dimensional model. In other words, based on the known viewpoint of each new image, the rays crossing of features of a device (e.g., a stent placed within the arteries) in the image provide two-dimensional x-ray data that is projected to the three-dimensional model. The missing depth data for each ray can then be recovered by the processor 30 from the intersection with the three-dimensional model. Registration errors are eliminated by constraining the rays to intersect with the vessels in the three-dimensional model, similar to the constraining of GPS-derived coordinates onto preliminarily-mapped streets. Such a registration provides anchor points on the three-dimensional vessel map, enabling a clinician to trace the path of a device (such as a stent) in the arteries, again while reducing the amount of radiation dose to the necessary minimum, e.g. to only where critical bifurcations may lead to a wrong navigation. The use of devices with wire push control enable even further reduction of dose and dye by adding information about the running length of the wire used to navigate the device at hand.

In some embodiments, the processor 30 registers a new image with a three-dimensional model by first identifying coronary arteries in the new image. The processor 30 then determines centerlines through the identified coronary arteries and determines sample points along the centerlines in the three-dimensional coordinate system of the model. The processor 30 next determines vascular geometric information for the sample points along the centerline. The processor 30 is configured to then determine a correspondence between the coronary arteries in the medical image and the three-dimensional model using at least the centerlines of the medical image and the centerlines of the three-dimensional model. The processor 30 may identify homologies between the centerlines of the model and the image, and determine if similar locations along the centerlines have the same coordinates. If there is at least some correspondence between the model and the image, the processor 30 is configured to update the three-dimensional model with the determined vascular geometric information from the medical image.

Figure 8:
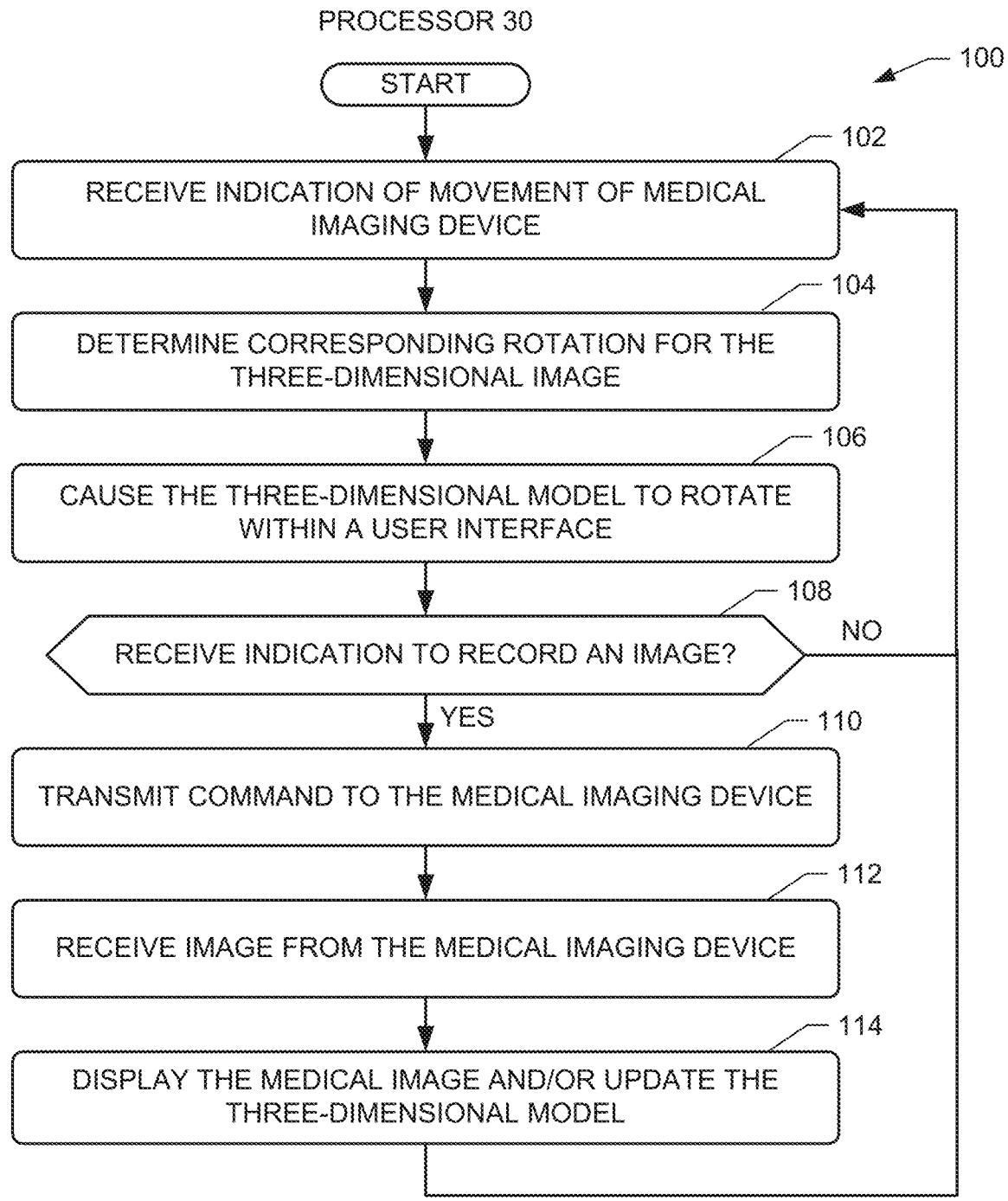
FIG. 8 is a flow diagram of an example procedure for causing a three-dimensional model to rotate based on detected rotation of a medical imaging device, according to an example embodiment of the present disclosure.

FIG. 8 is a flow diagram of an example procedure 100 for causing a three-dimensional model (such as the three-dimensional model 34 of FIG. 1) to rotate based on detected rotation of the medical imaging device 10, according to an example embodiment of the present disclosure. Although the procedure 100 is described with reference to the flow diagram illustrated in FIG. 8, it should be appreciated that many other methods of performing the steps associated with the procedure 100 may be used. For example, the order of many of the blocks may be changed, certain blocks may be combined with other blocks, and many of the blocks described may be optional. In an embodiment, the number of blocks may be changed based on how the synchronization is configured. The actions described in the procedure 100 are specified by one or more instructions that are stored in the memory device 32, and may be performed among multiple devices including, for example the processor 30 and/or the medical imaging device 10.

The example procedure 100 begins when the processor 30 receives an indication of movement of the medical imaging device 10 (block 102). The indication may include a digital message and/or analog signal indicative of relative or absolute angulation of the support structure 16. In some embodiments, the three-dimensional model may not be locked, such that movement of the medical imaging device 10 is disregarded or not used for synchronization by the processor 30. This enables the medical imaging device 10 to be rotated without affecting the display of the model on the display screen 28.

The processor 30 next determines, using the correlation file 40 (or transfer function), corresponding rotation for the synchronized three-dimensional medical image (block 104). The processor 30 then applies the determined rotation to the three-dimensional model such that it is rotated along its pitch and/or roll axes (block 106). The processor 30 also determines if an indication to record an image has been received (block 108). If an indication has not been received, the example processor 30 returns to block 102 for detecting additional rotation and/or movement of the medical imaging device 10.

However, if an indication to record an image is received, the processor 30 transmits a command or an instruction message to record an image (block 110). The processor 30 then receives the medical image after it is acquired (block 112). The processor 30 may then display the medical image in a user interface in conjunction with the three-dimensional model and/or update the three-dimensional model using the new image (block 114). The procedure 100 then returns to block 102 for detecting additional rotation and/or movement of the medical imaging device 10.

Physiological Index Calculation

Figure 9:
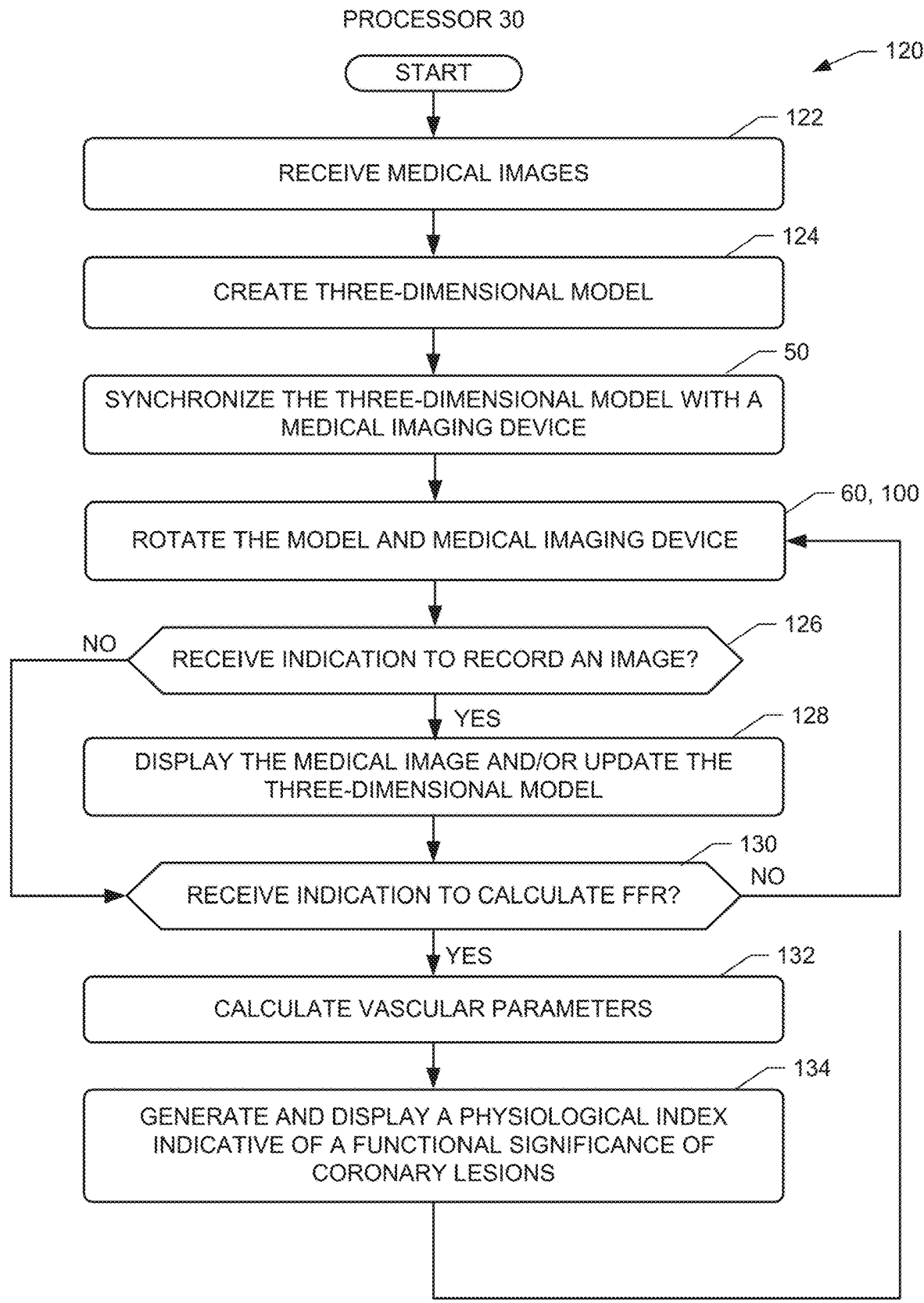
FIG. 9 is a flow diagram of an example procedure that uses synchronization between a medical imaging device and a three-dimensional model to generate a physiological index that is indicative of a functional significance of coronary lesions, according to an example embodiment of the present disclosure.

FIG. 9 is a flow diagram of an example procedure 120 that uses synchronization between a medical imaging device and a three-dimensional model to generate a physiological index that is indicative of a functional significance of coronary lesions, according to an example embodiment of the present disclosure. Although the procedure 120 is described with reference to the flow diagram illustrated in FIG. 9, it should be appreciated that many other methods of performing the steps associated with the procedure 120 may be used. For example, the order of many of the blocks may be changed, certain blocks may be combined with other blocks, and many of the blocks described may be optional. In an embodiment, the number of blocks may be changed based on how the synchronization is configured or the physiological index is determined. The actions described in the procedure 120 are specified by one or more instructions that are stored in the memory device 32, and may be performed among multiple devices including, for example the processor 30 and/or the medical imaging device 10.

Figure 10:
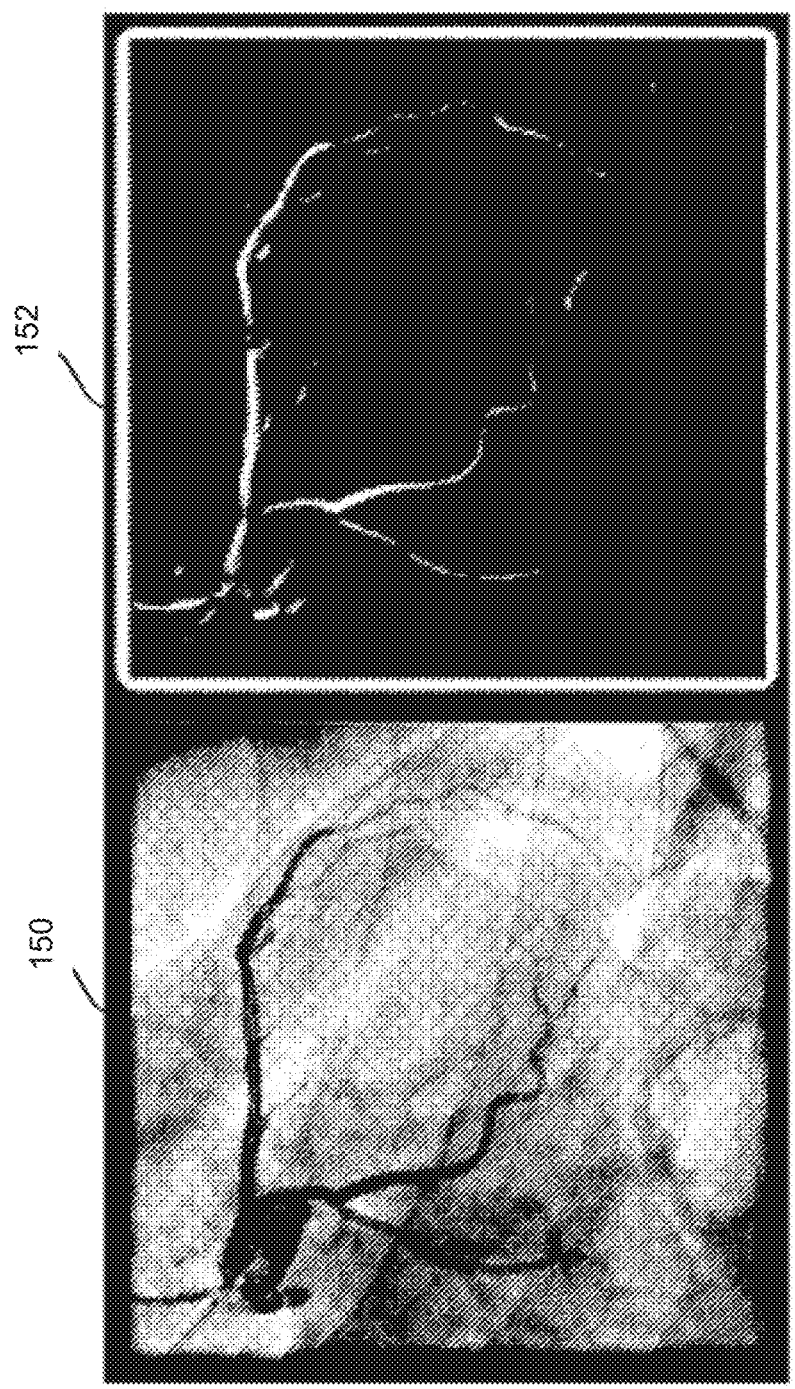
FIG. 10 shows an example image recorded by a medical imaging device and a Frangi-filter processed image, according to an example embodiment of the present disclosure.

The example procedure 120 may be carried out during a medical diagnosis of a patient's coronary arteries. The example procedure 120 may also be carried out during a medical treatment, such as placement of a stent or an inflation of a section of a patient's coronary arteries. The example procedure 120 begins when the processor 30 receives medical images from the medical imaging device 10 (block 122). In some embodiments, data images are simultaneously acquired from a plurality of vantage points, for example, 2, 3, 4 or more imaging vantage points. In some embodiments, images are acquired at a frame rate of, for example, 15 Hz, 30 Hz, or another lesser, greater, or intermediate frame rate. In some embodiments, the number of frames acquired per imaging vantage point is about 50 frames (200 frames total for 4 imaging vantage points). In some embodiments, the number of frames per imaging vantage point is, for example, 10, 20, 40, 50, 60, 100, or another larger, smaller, or intermediate number. In some embodiments, the number of heartbeat cycles comprised in an imaging period is about 3-4 heartbeat cycles. In some embodiments, the number of cardiac cycles is, for example, 3-4, 3-5, 4-6, 5-10, or another range of heartbeat cycles having the same, lesser, greater, or intermediate range boundaries. FIG. 10 shows an example image 150 recorded by the medical imaging device 10 and a Frangi-filter processed image 152, according to an example embodiment of the present disclosure. It should be noted that when using two or more 2-D projections of a patient's vessels, for example heart vessels, it is a potential advantage for two or more two-dimensional projections be taken at the same time, or at least at a same phase during a heartbeat cycle, so that the two-dimensional projections correspond to a similar vessel shape. Deviations between the two-dimensional projections might arise from cardiac, and/or respiratory and/or to patient motions between the two-dimensional projection frames. In some embodiments, to reduce deviations that might arise from lack of cardiac phase synchronization, an ECG output is used by the processor 30 to select a same cardiac phase in the two-dimensional projections frames. In some embodiments, two-dimensional projection frames are selected to be at an end of the diastole phase of the cardiac cycle. In some embodiments, the temporal and/or phase order in which two-dimensional projection frames are acquired is used to perform registrations among images taken during adjacent movement cycle phases. In some embodiments, images registered from a first phase to a second phase are then re-registered into a third and/or further phase, such that images take at widely separated heartbeat cycle phases can be registered to one another.

In some embodiments, the heart is imaged under the influence of intravenous adenosine, which potentially exaggerates a difference between normal and abnormal segments. Optionally imaging with and without adenosine potentially allows for the determination of the (vascular expanding) effects of adenosine itself, which in turn potentially provides information about vascular compliance and/or autoregulatory state.

After the images are received, in some embodiments, the processor 30 calculates a Hessian transform from every pixel of a Gaussian smoothed input image (the Hessian is related to the 2nd derivative of the image data, and is a form of edge detection). The Hessian-transformed image is smoothed, for example, by a Gaussian filter. The eigenvectors and eigenvalues of the smoothed Hessian-transformed image are calculated by the processor 30. The resulting eigenvalues are in general larger where the original image comprises edges, while eigenvectors corresponding to large eigenvalues describe the direction in which the edge runs.

In some embodiments, the processor 30 calculates a diffusion image. A finite difference scheme is used to perform the diffusion, using, in some embodiments, the eigenvectors as diffusion tensor directions. Additionally or alternatively, a Frangi filter is applied by the processor 30, based on the Hessian eigenvectors, which comprises computation of the likeliness of an image region to be within a vessel. By way of a non-limiting example, the Frangi-filter processed image 152 of FIG. 10 depicts the original image 150 after image enhancement using a Frangi filter. In some embodiments, another filter is used, for example a threshold filter, or a hysteresis threshold filter, whereby pixels of an image are identified as belonging within an image region of a vessel.

Figure 11:
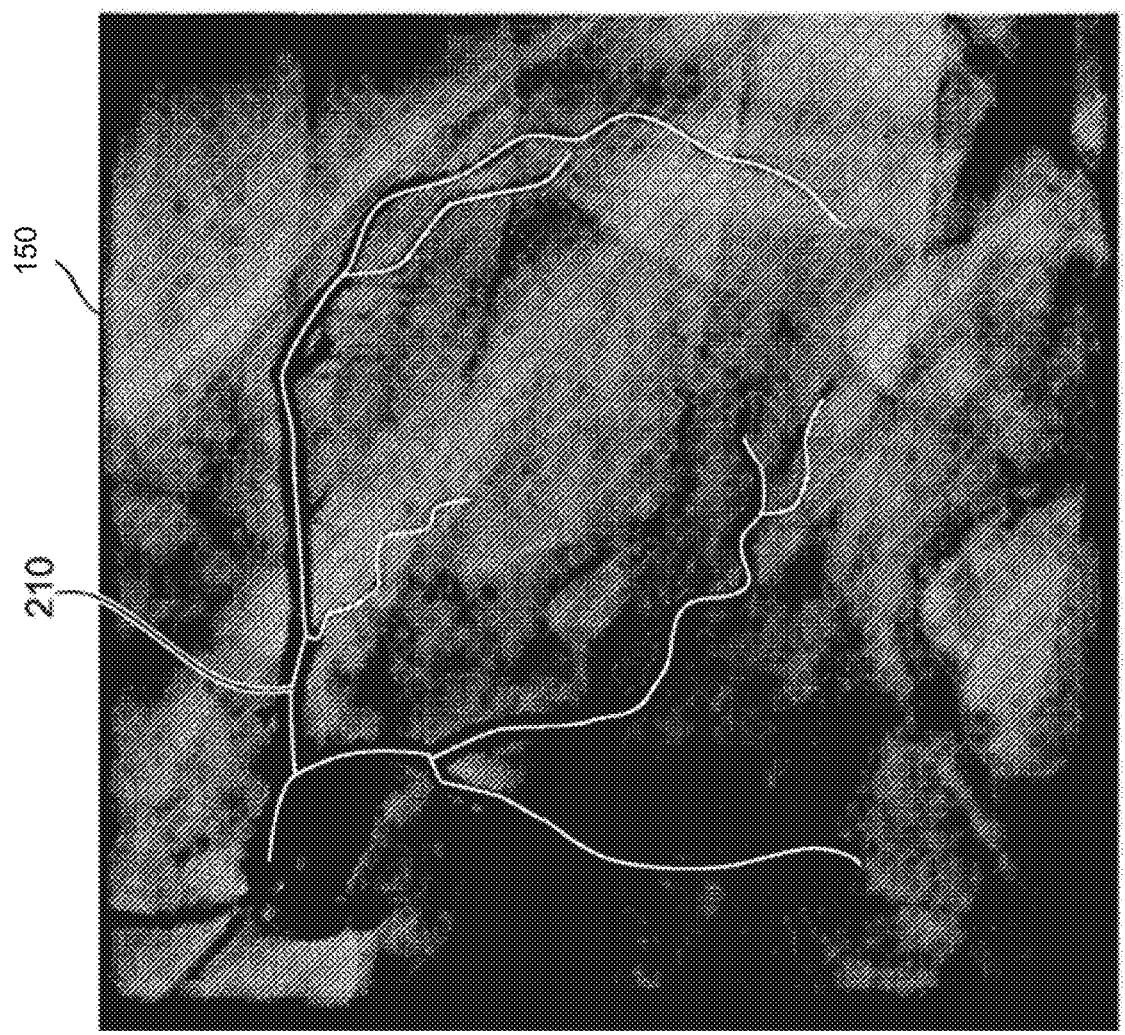
FIG. 11 shows an image after centerlines have been determined, according to an example embodiment of the present disclosure.

Further, in some instances, the processor 30 processes the images to generate a black-white figure representing vascular locations in an angiographic projection image. In some embodiments, a hysteresis threshold filter is performed on the Frangi filter output with high and low thresholds. First an algorithm performed by the processor 30 detects the pixels which are (for example, with reference to image 152) brighter than the higher threshold, which are labelled as vascular pixels. In a second step, the algorithm also labels as vascular those pixels with brightness higher than the low threshold, and also connected across the image to pixels already labeled as vascular pixels. Square dilation may also be performed on the black-white image, and the result is subtracted from the original black-white image. The subtraction image comprises a one pixel-wide frame along which the growth of the region of vascular-labelled pixels is then examined by the processor 30. The values (brightnesses) of the pixels in this frame are compared locally to those of existing vascular pixels, and to the surrounding. A high relative result leads to expansion. Optionally, the process repeats until no more vascular pixels are found. Further, in some embodiments, a thinning convolution is applied by the processor to thin the black-white image segments down to lines which represent the vascular centerlines. FIG. 11 shows the image 110 after centerlines 210 have been determined, according to an example embodiment of the present disclosure.

Returning to FIG. 9, the processor 30 uses the images to create a three-dimensional model (block 124). To create a three-dimensional model, the processor 30 identifies vessels in the images and extracts centerlines of those vessels. Vascular centerlines have several properties which make them a useful reference for other phases of vascular tree reconstruction. For instance, centerlines are features determinable from two-dimensional images, enabling their use to relate individual images to one another in three-dimensions. Further, vascular centerlines are, by definition, distributed throughout an imaging region of interest when the target is to reconstruct a three-dimensional vascular model. Moreover, vascular centerlines are extended features which preserve sufficient similarity among images, even images taken from different views, that their homologies are readily identifiable, for example in the two-dimensional images themselves, and/or by back-projection along rays into a 3-D space, where ray intersections (and/or intersections among dilated volumes based on back-projected rays) identify homologous targets found in different image projections. Additionally, centerlines comprise a convenient frame of reference for organizing and/or analyzing features related to position along a blood vessel. For example, using distance along the centerline as a reference, morphological features such as diameter, and/or functional features such as flow resistance, can be expressed as functions in a simplified, one-dimensional space. Also, intersections of centerlines provide a convenient way for the processor 30 to identify vascular branch points, and/or divide a vascular tree into distinct segments which are optionally treated separately from one another, and/or further simplified, for example, for purposes of the functional analysis of flow properties.

Additionally or alternatively, in some embodiments, another type of image feature is identified by the processor 30. Optionally, an image feature includes, for example, a furcation of a vessel, or a location of minimal radius (a locally reduced radius compared to surrounding vascular regions) in a stenosed vessel. Optionally, an image feature includes any configuration of image pixels having a pattern of intensities generally lacking in self-identity (below a predetermined threshold of self-identity, for example, always above a threshold of intensity difference, or always within a criterion for statistical insignificance of self-identity) over translation in any direction, for example, a corner-like bend or furcation.

Figure 12:
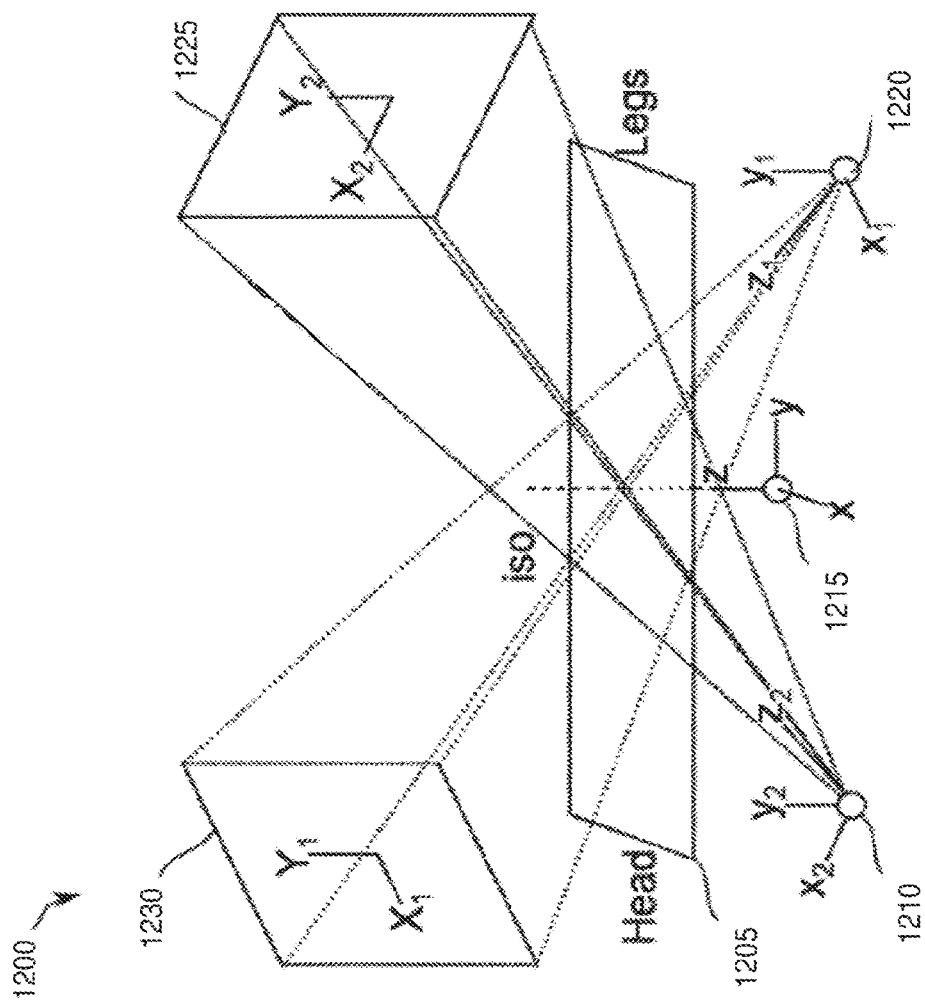
FIG. 12 shows a schematic of an exemplary arrangement of imaging coordinates for an imaging system, according to an example embodiment of the present disclosure.

FIG. 12 shows a schematic of an exemplary arrangement 1200 of imaging coordinates for an imaging system, according to an example embodiment of the present disclosure. Several different spatial relationships of an imaging arrangement are used in determining the 3-D relationship of image data in a set of 2-D images. In some embodiments, the image coordinate systems 1210 and 1220 and associated imaging planes 1225 and 1230 describe how images taken of the same subject at different positions relate to one another, information which is used to reconstruct three-dimensional information about a patient. In some embodiments of the invention, these coordinates reflect the axes of the C-arm rotations of the medical imaging device 10. In some embodiments, the coordinate plane 1215 of the patient (for example, lying on bed 1205) is also used as part of three-dimensional reconstruction.

The example processor 30 extracts centerlines of a vascular tree from the acquired two-dimensional images. In some embodiments, image filtering by anisotropic diffusion comprises a portion of the processing operations which precede centerline extraction. Anisotropic diffusion of two-dimensional gray-scale images reduces image noise while preserving region edges—smoothing along the image edges, and removing gaps due to noise.

After centerlines are extracted from the images and projected to a three-dimensional coordinate system, the example processor 30 determines centerline correspondences between the images. A goal of finding centerline correspondences is to find correspondences between different two-dimensional images (points that image the same region of space, though potentially from different angles), such that a three-dimensional reconstruction of the target vasculature can be made. As described below, the centerline correspondence determination may include motion compensation and/or imaging position artifact compensation.

With ideal calibration information (each image plane perfectly identified relative to a common coordinate axis, for example), and no artifacts due to motion or other positioning errors, back-projecting a large enough number of two-dimensional images to three-dimensional space potentially yields intersecting rays uniquely defining the extents of the vascular centerline in three-dimensions. In practice, deviations among images originate, for example, from breathing, voluntary movements of the patient, and inaccurate and/or imprecise phase-locking of imaging exposures to the cardiac cycle. Calibration errors potentially introduce other forms of image position artifacts.

For motion compensation, a subset of images (comprising a plurality) with identified two-dimensional centerlines is selected by the processor 30. The centerlines are optionally dilated, and a centerline projection back into a three-dimensional coordinate system may be performed based on the current best-known projection parameters for each image (initially these are, for example, the parameters expected based on the known calibrations of the imaging device). The resulting projected volume is skeletonized, in some embodiments, to form a "consensus centerline". The consensus centerline is projected back into the coordinate systems of two-dimensional images comprising those which were not used in forming the consensus centerline. An optimization procedure performed by the processor 30 adjusts projection parameters for the three-dimensional centerline into each two-dimensional image to fit more closely centerlines found within the image itself. This adjustment is used to adjust the projection parameters associated with each image.

In another embodiment for motion compensation, the processor 30 identifies features in a reference image R based on a feature detection method. Such an image feature is, for example, a furcation of a vessel, and origin of the coronary vessel tree, a location of minimal radius in a stenosed vessel, and/or any configuration of image pixels having a pattern of intensities generally lacking in self-identity over translation in any direction—for example, a corner-like bend or furcation. Similar features (putatively homologous to those of the reference image) are identified in remaining images F. In some embodiments, images in F are then registered to image R. For example, the best-known projection parameters of image F are used to transform into the best-known projection plane of image R, and then optimized to obtain an improved fit, for example using epipolar geometry to calculate parameters of shift, rotation, and/or scaling. Optionally, registration comprises application of a geometric distortion function. The distortion function is, for example, a first, second, or other-order function of the two image plane coordinates. Additionally or alternatively, the distortion function comprises parameters describing the adjustment of nodal points defined within the image coordinate planes to bring them into registration.

In some embodiments, the processor 30 calculates image correction parameters based on identified corresponding image features. Correction parameters typically describe, for example, translation and/or rotation of a system of coordinates of a particular image. Based on the calculated parameters, the angiographic images are registered to provide to provide mutual geometrically correspondence there amongst. In some embodiments, several images are registered relative to one of the images. For example, when corresponding image features are identified in N images (e.g., N=2, 3, 4 or more) one of the images can be selected as a reference, while the registration is applied for the remaining N−1 angiographic images such that each of those remaining images geometrically corresponds to the single angiographic image that was selected as a reference. In some embodiments, another registration scenario, for example, pairwise registration, is performed.

In some instances, the processor 30 may use a heart surface constraint for discarding bad ray intersections from calculated correspondences among images. In some imaging procedures, a "large enough" number of projections is potentially unavailable, such that the error in the determined position of ray intersections potentially prevents convergence to a correct output. In some embodiments, operations to reduce the effect of this source (and/or other sources) of positional error are performed by the processor 30, based on a heart surface constraint.

The processor 30 selects an image which comprises features expected to be within the projected outline of the heart. The features are representations of the coronary arteries, which course over the heart surface. In some embodiments, previously determined vascular centerlines comprise the identified features. A convex hull may be determined based on the vascular centerlines. This hull grossly represents the shape of the heart (where it is covered by identified artery centerlines) as projected into the plane of the selected two-dimensional image. The processor 30 may then determine the tree-dimensional hull position (heart shell) from the various available two-dimensional hull projections, for example by using the best-known projection parameters for each two-dimensional image plane, and/or the intersections of the three-dimensional polyhedra. Such a surface can be defined using any technique known in the art, including, without limitation, polyhedra stitching, based on the descriptions provided herein. The processor 30 may dilate the heart shell to a volume, the amount of dilation being determined, for example, as corresponding to an error limit, within which "true" vascular regions are expected to fall. The processor 30 may then exclude candidate 3-D positions of vascular centerline points which fall outside the heart shell.

Figure 13:
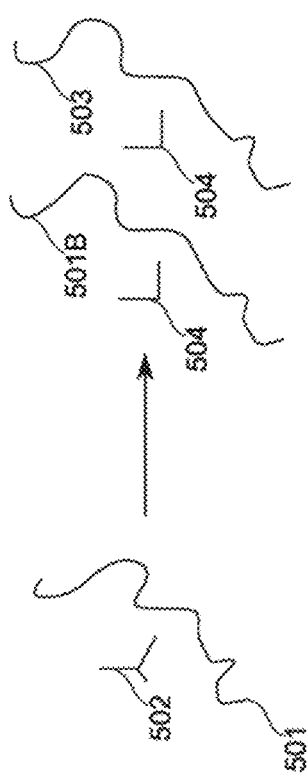
FIGS. 13 to 15 show diagrams illustrative of how centerline homologies are determined, according to an example embodiment of the present disclosure.
Figure 14:
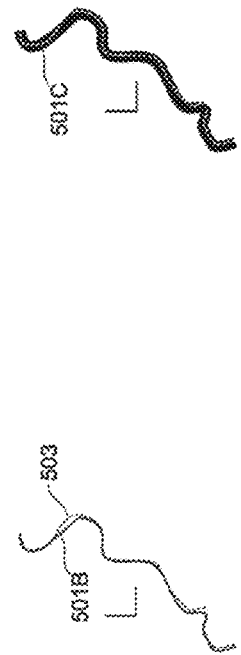

After providing image compensation, the processor 30 identifies homologies of the different image centerlines for creating a three-dimensional model. In an embodiment, the processor selects a base two-dimensional image for homology determination. The vascular centerlines in one of the remaining images is projected by the processor 30 into the plane of the base image. For example, exemplary vascular centerline 503 of FIG. 13 is from a base image having a base coordinate system 504. Vascular centerline 501, taken from another image having a different coordinate system 502 is shown transformed into coordinate system 504 (translated in one direction for clarity in FIG. 13) as centerline 501B. In FIG. 14, the two centerlines are shown overlaid, illustrating their general similarity, and some artificial differences where they diverge.

Figure 15:
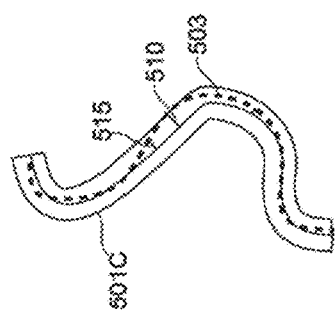

In some instances, the projected vascular centerline 501B is dynamically dilated by the processor to create centerline 501C, noting where intersections with the base image vascular centerline first occurs, and continuing, for example, until all homologies have been identified. Dynamic dilation comprises, for example, gradual expansion of the centerline, for example by application of a morphological operator to pixel values of the image. In some embodiments, another method, for example, a nearest-neighbor algorithm, is used (additionally or alternatively) to determine correspondences. FIG. 15 shows examples of correspondence between vascular centerline points at either end of minimal distance lines 515 and 510.

After homologies are identified between the centerlines, the processor 30 performs a three-dimensional mapping of two-dimensional centerlines. In some embodiments, mapping begins with identification of optimal projection pairs. Where several different images have been acquired, there are potentially several different (although homologous) projections of each region of a vascular centerline into three-dimensional space, each based on a different pair of two dimensional images. Initially, the processor 30 selects a segment comprising a vascular centerline in addition to with an initial homologous group of centerline points along it (for example, a point from an end) in the different two-dimensional images.

Figure 16:
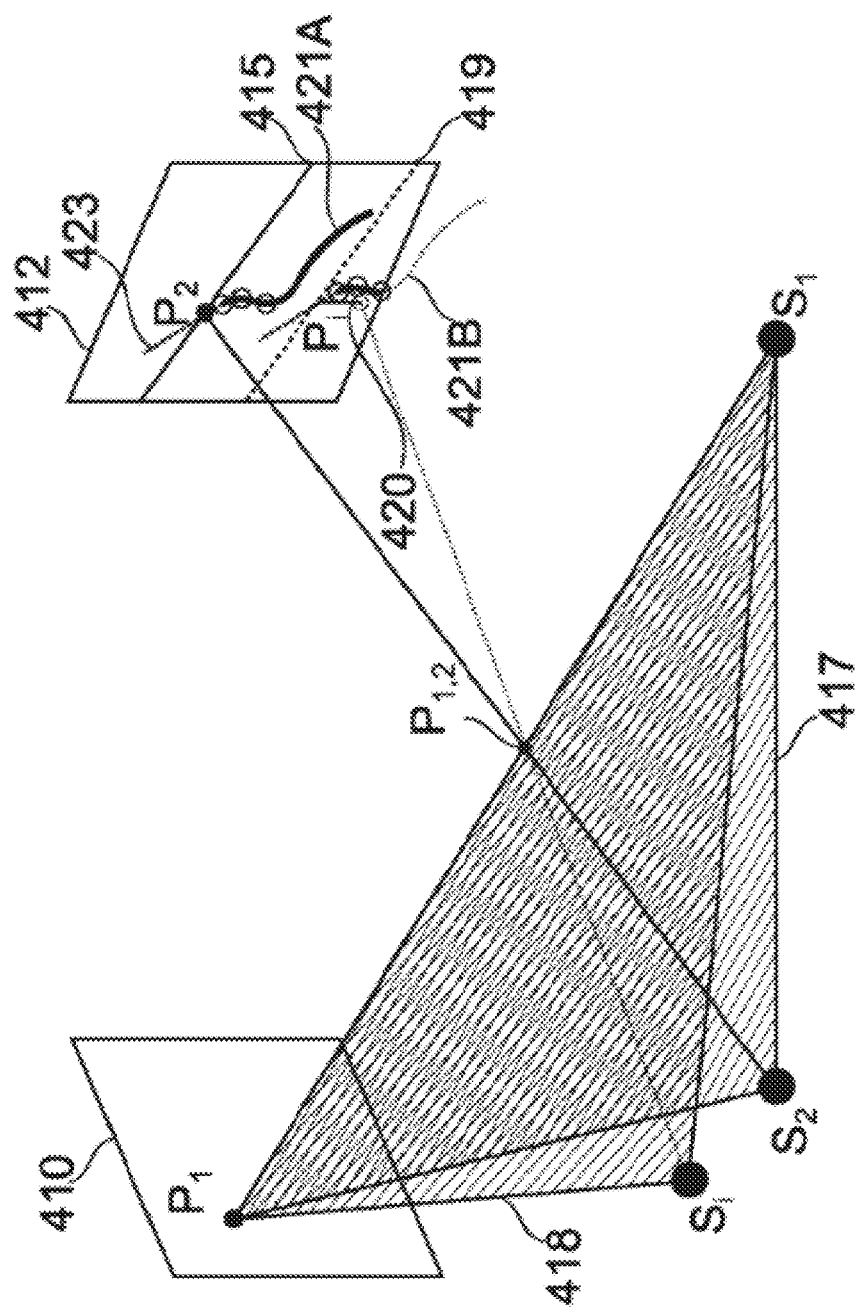
FIG. 16 shows a schematic representation of epipolar determination of three-dimensional target locations from two-dimensional image locations and their geometrical relationships in space, according to an example embodiment of the present disclosure.

As shown in FIG. 16, a point $P_1$ on a vascular centerline (corresponding to some homologous group of centerline points P) is selected from a first base image. Other points $P_2 \ldots P_N$ are then selected from the homologous group P to be paired with $P_1$ to find a position in three-dimensional space. FIG. 16 shows a schematic representation of epipolar determination of three-dimensional target locations from two-dimensional image locations and their geometrical relationships in space, according to an example embodiment of the present disclosure. A point $P_1$, associated with image plane 410 is matched to a point $P_2$ to determine a location $P_{1,2}$ in three-dimensional space, using principles of epipolar geometry. In brief: the ray passing from a source $S_1$ through a target region to point $P_1$ is on a plane 417 which is determined also by rays passing from $S_2$ to intersect it. The continuations of these rays intersect plane 412 along an epipolar line 415.

The processor 30 then evaluates points for their relative suitability as the optimal available projection pair to extend a vascular centerline in three-dimensional space. In some embodiments, a criterion for the optimal choice of a projection point is a distance of a projected point from its associated epipolar line. Ideally, each point $P_2 \ldots P_N$ lies on the epipolar line corresponding to the epipolar plane defined by $S_2 \ldots S_N$. However, due to imaging position artifacts—for example, those described in relation to calibration and/or motion—there may remain some error, such that a point $P_j$, previously determined to be homologous to $P_1$, lies off of its associated epipolar plane 418, and therefore a distance 420 away from its associated epipolar line 419. Optionally, the projection point closest to its associated epipolar line for a given homology group is scored as most suited as the projection point for extending the vascular centerline.

In some embodiments, one or more criteria for the optimal choice of a projection point relate to the continuity of extension that a projected point provides from projected points already determined. For example, a set of points along vascular centerline 421A, 421B can be used to determine a current direction of extension 423, and/or expected distance interval to the next extending point in three-dimensional space. In some embodiments, projection points which more closely match one or more of these, or another geometrical criterion, are scored as correspondingly more suitable choices.

The processor 30 next determines whether a different base point in the homology group should be chosen. If yes, the next base point is chosen, and further projections and evaluations continue. If no, the point having the optimal (most suited from among the available choice) score for inclusion in the three-dimensional vascular centerline is chosen. In some embodiments, the current vascular segment centerline is extended according to point specified by the identified optimal pair of projections. Vascular centerline determination continues, in some embodiments, where it is determined whether or not another sample (homology group) should be assessed for the current vascular centerline. If so, operations continue by selection of the next sample. If not, determination is made whether the last vascular segment centerline has been determined. If not, the next segment is selected, and processing continues at the first sample of that segment. If yes, the processor 30 is then able to determine vascular geometric information.

The example processor 30 determines vascular geometric information, such as vessel diameter across sample points of a selected two-dimensional projection, and extrapolated to the whole circumference of the blood vessel. In some embodiments, diameters across a plurality of projection angles are determined. In some embodiments, the projected view is selected from a single acquired image, optionally an image where the vessel is seen at its longest, and/or visible free of crossings. Optionally, the projected view is synthesized from two or more 2-D images.

To determine a diameter, the processor 30 determines an edge graph. For instance, a 2-D centerline projection is chosen which is mapped to locations relative to the locations of intensity values of the two-dimensional imaging data. Optionally, the projection selected by the processor 30 is one in which the blood vessel is projected at a maximum length. Optionally, the projection selected is one in which the blood vessel does not cross another vessel. In some embodiments, projections are chosen according to sub-regions of a two-dimensional centerline of a vascular segment, for example, to have maximum length and/or non-crossing properties within the sub-region. In some embodiments, images from orthogonal projections (and/or projections having another defined angular relationship) are selected.

The processor 30 may next estimate a starting vascular width (a radius, for example). The starting width is determined, for example, by generating an orthogonal profile to the centerline and identifying a peak of a weighted sum of the first and second derivatives of the image intensity along the profile. The processor 30 builds an orthogonal profile for points along the centerline; for example, for points sampled at intervals approximately equivalent to the vascular starting width. The precise choice of interval is not critical: using the radius as the interval is generally appropriate to provide a sufficient resolution for diameter estimation. Orthogonal profiles for sampled points are assembled by the processor 30 in a rectangular frame, somewhat as though the convolutions of the three-dimensional centerline were straightened, bringing the orthogonal profiles through the centerline into parallel alignment.

The example processor 30 may then determine connected routes along vascular edges. For instance, a first side (vascular edge) is chosen for route tracing. In some embodiments, a route is found by the processor 30 along the edge at approximately the distance of the initial radius, for example, by minimizing the energy that corresponds to a weighted sum of the first and second horizontal derivatives, optionally with the aid of an algorithm of the Dijkstra algorithm family. The processor 30 may reset centerline to the middle of the two vascular walls just determined. At this point, a three-dimensional model of a vascular tree includes centerlines specified by three-dimensional coordinates and diameters or other vascular geometric information.

In some embodiments, the processor 30 may divide the three-dimensional model into segments or branches, where a branch is defined as a section of a vessel (along the frame of reference established by the vascular centerline, for example) between bifurcations. The branches are numbered, for example, according to their generation in the tree. Branch points (nodes), in some embodiments, are determinable from points of the skeletal centerline representation which connect in more than two directions. In some embodiments, branch topology comprises division of a vascular tree model into distinct branches along the branch structure. In some embodiments, branch topology comprises recombination of branches, for example, due to collateral and/or shunting blood vessels.

In some embodiments, during a reconstruction process of the centerlines into a three-dimensional model, spatial location and radius of segments on each branch are sampled every small distance, for example every 1 mm, or every 0.1 mm to every 5 mm. In some embodiments, tree branches, corresponding to vessel segments between modeled bifurcations, correspond to vessel segments of a length of 1 mm, 5 mm, 10 mm, 20 mm, 50 mm, and even longer. In some embodiments, sampling every small distance increases the accuracy of a geometric model of the vessels, thereby increasing accuracy of flow characteristics calculated based on the geometric measurements. In some embodiments, the tree model is a reduced tree, limited to a single segment of a vessel, between two consecutive bifurcations of the vascular system. In some embodiments, the reduction is to a region of a bifurcation, optionally comprising a stenosis.

Returning to FIG. 9, after the three-dimensional model is created, the processor 30 synchronizes the model with the medical imaging device, as described above in connection with the procedure 50 of FIG. 5. After synchronization, the displayed three-dimensional model of a patient's coronary arteries is configured to rotate in correspondence with rotation of the medical imaging device, and vice versa, as described in connection with the procedures 60 and 100 respectively of FIGS. 6 and 8. While the model and imaging device are synchronized, the processor 30 determines if an indication to record an image is received (block 126). If an indication is received, the processor 30 receives the recorded image. The processor 30 may then display the medical image in a user interface in conjunction with the three-dimensional model and/or update the three-dimensional model using the new image (block 128).

The processor 30 next determines if a request has been received to calculate FFR values or another physiological index indicative of vascular function (block 130). If a request has not been received, the procedure 120 returns to rotate the three-dimensional model in correspondence with rotation of the medical imaging device, and vice versa, as described in connection with the procedures 60 and 100 respectively of FIGS. 6 and 8. However, if the request has been received, the example processor 30 calculates vascular parameters from the three-dimensional model (block 132). The processor 30 then generates and displays a physiological index that is indicative of functional significance of coronary lesions (e.g., FFR values). The FFR values, as shown in FIG. 7, may be color coded and displayed in conjunction with the three-dimensional model. The procedure 120 returns to rotate the three-dimensional model in correspondence with rotation of the medical imaging device, and vice versa, as described in connection with the procedures 60 and 100 respectively of FIGS. 6 and 8

FFR indicates differences in flow between a vascular model of a potentially stenotic vasculature, and a different vascular model derived from and/or homologous to the stenotic vasculature model. In some embodiments, changes to create an astenotic version of the vascular model comprise determinations of wall opening (widening) in stenotic regions based on reference width measurements obtained in one or more other portions of the vasculature. In some embodiments, reference width measurements are obtained from vascular portions on either side of a stenosis. In some embodiments, reference width measurements are obtained from a naturally astenotic vessel at a similar branch order to a stenotic segment.

In some embodiments, the FFR index comprises a ratio of flow in model comprising a potentially stenotic vascular segment to a model wherein said segment is replaced by a lower flow-resistance segment, and/or the resistance to flow due to said segment is removed. A potential advantage of this ratio determination is that the index comprises an expression of the effect of a potential therapeutic treatment to a vasculature, for example, an opening of a vascular region by percutaneous coronary intervention ("PCI") such as stent implantation. Another potential advantage of this ratio is that it measures a parameter (fractional flow reserve) which, though well-accepted as providing an indication of a need for revascularization, is commonly determined in the art by invasive pressure measurements requiring direct access to both sides of stenotic lesion.

In some embodiments, a second model is constructed from the three-dimensional model. The second model optionally describes an at least partially healthier vascular system corresponding to the three-dimensional model. In some embodiments, the second model is constructed by changing a stenosis in the first model to be more open, as it would be if a stent were to open the stenosis; and in some embodiments the second model is constructed by choosing a section of a patient's vascular system which includes a healthy vessel similar to the problem vessel of the first model, and using it to replace a stenosed vessel. In some instances, a smoothing or normalization of the entire three-dimensional model is carried out such that specific targeting of a stenosis region is not necessary.

In some embodiments, an index indicative of the need for revascularization is calculated. This can be done based on the three-dimensional model or based on a comparison between the three-dimensional model and the second model of the vascular flow. The index is optionally used similarly to the pressure measurement-derived FFR index, to assess whether a stenosed vessel affects flow in the vascular system to such an extent that the prognosis for improvement in the subject's condition following inflation of the stenosed vessel is higher than the likelihood for complications resulting from the inflation itself.

The terms "FFR" and "FFR index" in all their grammatical forms are used throughout the present specification and claims to stand for the above-mentioned index, and not only for the FFR index mentioned in the Background section as an invasive measurement involving insertion of a guidewire equipped with a miniature pressure transducer across the stenosis. In some instances—in particular where distinctions among specific types of FFR and FFR-like indices are discussed—a subscript is used to distinguish them, for example $FFR_{pressure}$ for FFR derived from pressure measurements, and/or $FFR_{flow}$ where FFR is expressed in terms of flow determinations.

In some embodiments, the index is calculated based on a volume or other vascular parameter of a crown in the stenotic model and on a contribution of a stenosed vessel to the resistance to blood flow in the crown. In some embodiments, the FFR index is calculated as a ratio of flow resistance of a stenosed vessel in a vascular model which includes the stenosed vessel to flow resistance of an inflated version of the same vessel in a similar vascular model where the stenosed vessel was mathematically inflated. In some embodiments, the index is calculated as a ratio of flow resistance of a stenosed vessel in a vascular model to flow resistance of a neighboring similar healthy vessel in the vascular model. In some embodiments, the ratio is multiplied by a constant which accounts for different geometries of the stenosed vessel and the neighboring vessel.

In some embodiments, to evaluate an FFR index in a stenosed branch of a vessel tree, a one dimensional model of the vessel tree is created by the processor 30 to estimate a flow in the stenosed branch before and optionally also after (virtual) stent implantation. In some embodiments, in order to evaluate an FFR index in a stenosed branch of a vessel tree, a one dimensional model of the vessel tree is used to estimate the flow in the stenosed branch before and optionally also after stenosis inflation. Based on maximal peak flow of 500 mL/min and artery diameter of 5 mm, a maximal Reynolds number of the flow is:

$$\mathrm{Re}_{peak\_flow} = \frac{4Q_{peak\_flow}}{\pi d_{max} v} = \frac{4 \cdot 500_{mL/min}}{\pi \cdot 5_{mm} \cdot 3.5_{cP}} \approx 600 \qquad \text{Equation 5.1}$$

The above calculation assumes laminar flow. In laminar flow it is assumed, for example, that blood is a Newtonian and homogenous fluid. Another assumption which is optionally made is that flow in vessel branches is 1-D and fully developed across the cross section of the vessel.

Based on the assumptions, a pressure drop in each segment of a vessel tree is approximated according to Poiseuille formulation in straight tubes:

$$\Delta P_i = \frac{128 \mu L_i}{\pi \cdot d_i^4} Q_i = \Re_i Q_i \qquad \text{Equation 5.2}$$

Where $\Re_i$ is a viscous resistance to flow of a segment of the vessel. Minor losses, due to bifurcations, constrictions and curvatures of the vessels are optionally added as additional resistances in series, according to the Darcy-Weisbach formulation:

$$\Delta p = \frac{\rho V^2}{2} \cdot \sum K_i = \frac{8 \rho Q^2}{\pi^2 d^4} \cdot \sum K_i \qquad \text{Equation 5.3}$$

$$\Re(Q) = \frac{\Delta p}{Q} = \left( \frac{8\rho}{\pi^2 d^4} \cdot \sum K_i \right) \cdot Q \qquad \text{Equation 5.4}$$

where $K_i$ are corresponding loss coefficients. The resistance of a branch to flow is calculated as the sum of the individual resistances of segments along the branch:

$$\Re_{branch} = \int_L \frac{8\mu}{\pi r^4} dl = \frac{8\mu}{\pi} \int_L \frac{dl}{r(l)^4} \qquad \text{Equation 5.5}$$

-continued
or $$\Re_{branch} = \frac{8 \times 0.035_{g/cm \cdot s}}{\pi} \sum \frac{dl_i}{r_i^4} \qquad \text{Equation 5.6}$$

Figure 17:
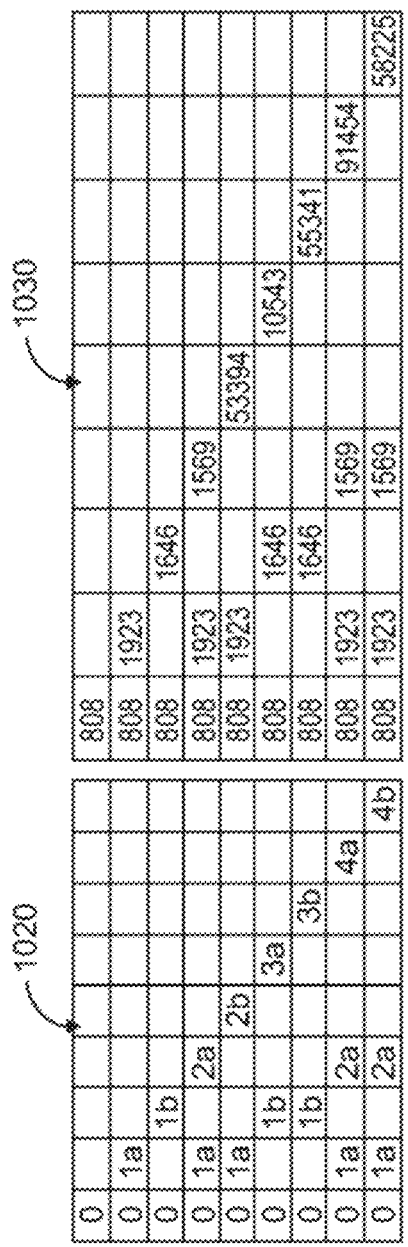
FIG. 17 shows a diagram of a resistance array of a three-dimensional vascular tree model, according to an example embodiment of the present disclosure.
Figure 17:
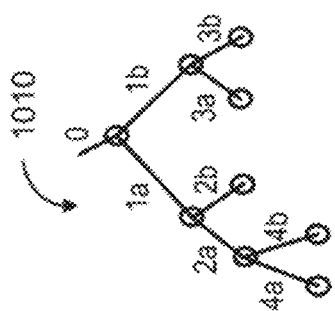
Figure 17:
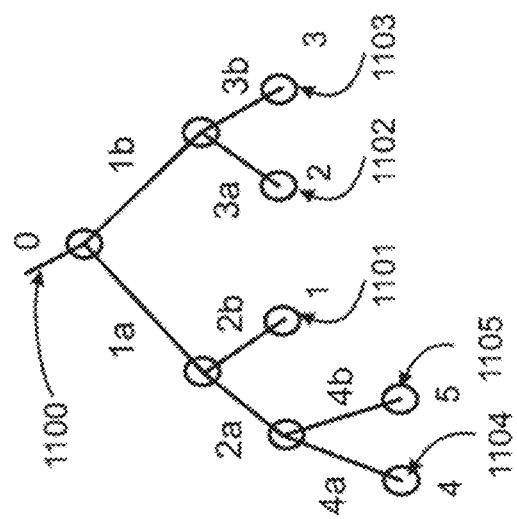

In an example, a resistance array corresponding to the example depicted in FIG. 17:

$\Re_s$=[808 1923 1646 1569 53394 10543 55341 91454 58225], where the resistance to flow is in units of mmHg*s/mL. The above resistance array is for a vessel with stenosis, as evidenced by a peak of 91454 [mmHg*s/mL] in the resistance array. A resistance array for a tree model without stenosis is optionally calculated, based on Quantitative Coronary Angiography ("QCA") methods for removing stenoses greater than 50% in area. In some embodiments, a tree model without stenosis is optionally calculated by replacing a stenosed vessel by an inflated vessel, that is, geometric measurements of a stenosed vessel section are replaced by measurements appropriate for an inflated vessel. In some embodiments geometric data (diameter and/or cross-sectional area) which is used for the inflated vessel is a maximum of the geometric data of the unstenosed vessel at a location just proximal to the stenosed location and at a location just distal to the stenosed location. In some embodiments geometric data (diameter and/or cross-sectional area) which is used for the inflated vessel is a minimum of the geometric data of the unstenosed vessel at a location just proximal to the stenosed location and at a location just distal to the stenosed location.

In some embodiments geometric data (diameter and/or cross-sectional area) which is used for the inflated vessel is an average of the geometric data of the unstenosed vessel at a location just proximal to the stenosed location and at a location just distal to the stenosed location. In some embodiments geometric data (diameter and/or cross-sectional area) which is used for the inflated vessel is calculated as a linear function of the geometric data of the unstenosed vessel between a location proximal to the stenosed location and a location distal to the stenosed location, that is, the inflated value is calculated taking into account distances of the stenosed location from the proximal location and from the distal location. A stented, also termed inflated, resistance array for the example is shown below:

$\Re_n$=[808 1923 1646 1569 53394 10543 55341 80454 51225]. The peak resistance, which was 91454 [mmHg*s/mL], is replaced in the inflated, or stented model, by 80454 [mmHg*s/mL].

FIG. 17 also depicts a coronary tree model 1010, a combination matrix 1020 depicting tree branch tags, and a combination matrix 1030 depicting tree branch resistances, all produced according to an example embodiment. The tree model is an example tree model with nine branches, tagged with branch numbers 0, 1a, 1b, 2a, 2b, 3a, 3b, 4a and 4b. The combination matrix 1020 includes nine rows, which contain data about nine stream lines, that is, nine paths through which fluid can flow through the tree model. Five of the rows include data for five full stream lines, in darker text, for five paths which go a full way to outlets of the tree model. Four of the rows include data for partial streamlines, in lighter text, for four paths which are not fully developed in the tree model, and do not go a full way to outlets of the tree model. The combination matrix 1030 depicts rows for the same tree model as depicted in the combination matrix 1020, with branch resistances located in matrix cells corresponding to branch tags in the combination matrix 1020.

After calculating a resistance of each branch, stream lines are defined from the tree origin, branch 0 to each outlet. To keep track of the stream lines, branches which constitute each stream line are listed in a combination matrix. In some embodiments, defined stream lines are also numbered, as shown in FIG. 17. As shown in FIG. 17, a tree model 1100 of a vascular system is provided with tags 1101 to 1105 numbering outlets of the tree model 1100, produced according to an example embodiment of the invention, the tags corresponding to stream lines. A pressure drop along a stream line j is calculated as a sum of pressure drops at each of its component branches (i), according to:

$$dp_j = \sum \mathfrak{R}_i Q_i \qquad \text{Equation 5.7}$$

when each branch has a different flow $Q_i$.

Based on a principle of mass conservation at each bifurcation, the flow rate in a mother branch is the sum of flow rates of daughter branches. For example:

$$Q_{1a} = Q_{2a} + Q_{2b} = Q_{4a} + Q_{4b} + Q_{2b} \qquad \text{Equation 5.8}$$

Thus, for example, a pressure drop along a stream line which ends at branch 4a is:

$$dp_{4a} = \mathfrak{R}_0 Q_0 + \mathfrak{R}_{1a} Q_{1a} + \mathfrak{R}_{2a} Q_{2a} + \mathfrak{R}_{4a} Q_{4a} = \qquad \text{Equation 5.9}$$

$$= \mathfrak{R}_0 (Q_{4a} + Q_{4b} + Q_{2b} + Q_{3a} + Q_{3b}) +$$

$$\mathfrak{R}_{1a}(Q_{4a} + Q_{4b} + Q_{2b}) + \mathfrak{R}_{2a}(Q_{4a} + Q_{4b}) + \mathfrak{R}_{4a} Q_{4a} =$$

$$= Q_{4a}(\mathfrak{R}_0 + \mathfrak{R}_{1a} + \mathfrak{R}_{2a} + \mathfrak{R}_{4a}) + Q_{4b}(\mathfrak{R}_0 + \mathfrak{R}_{1a} + \mathfrak{R}_{2a}) +$$

$$Q_{2b}(\mathfrak{R}_0 + \mathfrak{R}_{1a}) + Q_{3a}\mathfrak{R}_0 + Q_{3b}\mathfrak{R}_0 =$$

$$= Q_4 ER_{4,4} + Q_5 ER_{4,5} + Q_1 ER_{4,1} + Q_2 ER_{4,2} + Q_3 ER_{4,3}$$

where $Q_j$ is a flow rate along stream line j, and $ER_{4,j}$ is a sum of common resistances of stream line j and stream line 4. A global expression is optionally formulated for the pressure drop along stream line j:

$$dp_j = \Sigma Q_i ER_{i,j} \qquad \text{Equation 5.10}$$

For a tree with k outlet branches, that is, for k full stream lines, a set of k linear equations are optionally used:

$$\begin{bmatrix} ER_{11} & ER_{12} & \ldots & \ldots & ER_{1k} \\ ER_{21} & ER_{22} & \ldots & \ldots & ER_{2k} \\ \ldots & & & & \\ ER_{k1} & ER_{k2} & \ldots & \ldots & ER_{kk} \end{bmatrix} \begin{bmatrix} Q_1 \\ Q_2 \\ \ldots \\ Q_k \end{bmatrix} = \begin{bmatrix} dp_1 \\ dp_2 \\ \ldots \\ dp_k \end{bmatrix} \qquad \text{Equation 5.11}$$

$$\overline{\overline{A}} \times \overline{Q} = \overline{DP}$$

where indices 1 . . . k represent stream lines in the tree, and $Q_1 \ldots Q_k$ represent flow rates at corresponding outlet branches. The k×k matrix A consists of elements ER and is calculated from the combination matrix. For example, for the 5 stream lines tree shown in FIG. 6, the ER matrix is:

$$ER = \begin{bmatrix} \mathfrak{R}_0 + \mathfrak{R}_{1a} + \mathfrak{R}_{2b} & \mathfrak{R}_0 & \mathfrak{R}_0 & \mathfrak{R}_0 + \mathfrak{R}_{1a} & \mathfrak{R}_0 + \mathfrak{R}_{1a} \\ \mathfrak{R}_0 & \mathfrak{R}_0 + \mathfrak{R}_{1b} + \mathfrak{R}_{3a} & \mathfrak{R}_0 + \mathfrak{R}_{1b} & \mathfrak{R}_0 & \mathfrak{R}_0 \\ \mathfrak{R}_0 & \mathfrak{R}_0 + \mathfrak{R}_{1b} & \mathfrak{R}_0 + \mathfrak{R}_{1b} + \mathfrak{R}_{3b} & \mathfrak{R}_0 & \mathfrak{R}_0 \\ \mathfrak{R}_0 + \mathfrak{R}_{1a} & \mathfrak{R}_0 & \mathfrak{R}_0 & \mathfrak{R}_0 + \mathfrak{R}_{1a} + \mathfrak{R}_{2a} + \mathfrak{R}_{4a} & \mathfrak{R}_0 + \mathfrak{R}_{1a} + \mathfrak{R}_{2a} \\ \mathfrak{R}_0 + \mathfrak{R}_{1a} & \mathfrak{R}_0 & \mathfrak{R}_0 & \mathfrak{R}_0 + \mathfrak{R}_{1a} + \mathfrak{R}_{2a} & \mathfrak{R}_0 + \mathfrak{R}_{1a} + \mathfrak{R}_{2a} + \mathfrak{R}_{4b} \end{bmatrix} \qquad \text{Equation 5.12}$$

$$ER = \begin{bmatrix} 56125 & 808 & 808 & 2731 & 2731 \\ 808 & 12997 & 2454 & 808 & 808 \\ 808 & 2454 & 57795 & 808 & 808 \\ 2731 & 808 & 808 & 95754 & 4300 \\ 2731 & 808 & 808 & 4300 & 55525 \end{bmatrix} \qquad \text{Equation 5.13}$$

In some embodiments, fluid pressure measurements are made, for example blood pressure measurements. Based on provided fluid pressure boundary conditions ($P_{in}$ and $P_{out\_i}$), a vector $\overline{DP}$ is defined, and $Q_i$ is calculated:

$$\overline{Q} = \overline{\overline{A}}^{-1} \times \overline{DP} \qquad \text{Equation 5.14}$$

For example, for a constant pressure drop of 70 mmHg between the origin and all the outlets, the following flow distribution between the outlets is calculated:

Q=[1.4356, 6.6946, 1.2754, 0.7999, 1.4282], where the units of flow are mL/s.

In some embodiments, two models of a tree are calculated—a first model with stenoses, optionally as measured for a specific patient, and a second model without stenoses. FFR is calculated for each branch using the formula:

$$FFR = \frac{Q_S}{Q_N} \qquad \text{Equation 5.15}$$

For example, for the tree described above, the FFR calculated for each one of the 9 branches is:

FFR=[1.00 1.00 1.00 1.00 1.00 1.00 1.00 0.8846 0.8874]

It should be emphasized that the above-calculated FFR, expressed directly in terms of flows $Q_S$, $Q_N$ ($FFR_{flow} = Q_S/Q_N$), is distinct in its determination from the pressure measurement-derived FFR ($FFR_{pressure} = P_d/P_a$), calculated based on pressure differences distal $P_d$ and proximal $P_a$ to a stenosis. Furthermore, rather than being a comparison of two variables of a fixed system state, it is a comparison of two distinct states of the system.

For FFR$_{pressure}$, a finding of a large difference in pressure measurements across a stenotic lesion (for example, FFR$_{pressure}$≤0.75) suggests that removing the lesion would remove a substantial resistance ℜ to flow, whereby blood flow, in turn, would substantially increase. "Substantially", in this case, means "enough to be medically worthwhile". This chain of reasoning relies on simplifying assumptions about remaining pressures and resistances in the vascular system different in detail from those recited hereinabove in relation to FFR$_{flow}$.

Nevertheless, the two indices are closely related in what they describe. FFR as such—although it is commonly measured by pressure differences in a fixed system state—is defined as the ratio of maximum blood flow in a stenotic artery to maximum blood flow if the same artery were normal. Thus, FFR$_{flow}$ and FFR$_{pressure}$ may be characterized as differently arrived-at indexes of the same desired information: what fraction of flow can be restored, at least in principle, by intervention at a particular region of the cardiac vasculature.

Also, as for FFR$_{pressure}$, a goal of determining FFR$_{flow}$, in some embodiments, is the guidance of medical decision making by providing a rapidly calculable, easily interpreted, index. It is potentially sufficient for a medical professional seeking diagnostic assistance to establish by a vascular index such as FFR$_{flow}$ that intervention will make a medically meaningful change in perfusion. A ratio index is exemplary of an index that compactly expresses such change. It should also be noted that by describing an index that expresses a potential for change, FFR$_{flow}$, like FFR$_{pressure}$ itself, potentially reduces the effects of errors and/or distraction in the absolute determination of vascular perfusion characteristics.

In embodiments in which the vascular function index is calculated based only on the stenotic model, the resistance ℜ$_S$ contributed by a stenosis to the total resistance of the lesion's crown is evaluated. The volume V$_{crown}$ of the crown distal to the stenosis is also calculated. An FFR index (FFR$_{resistance}$) can then be calculated as a function which decreases with ℜ$_S$ and V$_{crown}$. A representative example of such a function includes, without limitation, $$FFR = \left(1 + \frac{\Re_S k V_{crown}^{3/4}}{P_a - P_0}\right)^{-1}$$ Equation 5.15a where P$_a$ is the aortic pressure, P$_0$ is the pre-capillary pressure and k is a scaling law coefficient which can be adapted to the aortic pressure. A flow analysis of blood flow and optionally arterial pressure along a segment of interest, based on the tree model and optionally on other available hemodynamic measurements, such as aortic pressure and/or amount of injected contrast.

The example embodiment just described potentially provides a minimally-invasive physiological index indicative of functional significance of coronary lesions. The example method is optionally performed during a coronary angiography procedure, and calculations are optionally performed during the coronary angiography procedure, such that the minimally-invasive physiological index is provided in real-time.

In an example implementation, given a proximal arterial pressure, P$_a$, [mmHg], flow rate through a segment of interest Q$_s$, [mL/s] is optionally derived from a concentration of iodine contrast material, based on an analysis of concentration-distance-time curves, and a geometric description of the segment of interest, including diameter d(l) [cm], and/or volume V(l) [ml] as a function of segment length.

In some embodiments, especially in case of large vessels such as the Left Anterior Descending coronary artery (LAD), blood flow can be measured for obtaining a flow model using a transthoracic echo Doppler, or other modalities such as MRI or SPECT. For a given segment, a total resistance of the segment (R$_t$, [mmHg*s/mL]) is optionally calculated by dividing arterial pressure by flow rate:

$$R_t = \frac{P_a}{Q_s}$$ Equation 5.16 where R$_t$ corresponds to total resistance, P$_a$ corresponds to arterial pressure, and Q$_s$ corresponds to flow rate through the vessel segment. From geometric description of the segment, a local resistance of the stenosis in the segment R$_s$, [mmHg*s/mL] is estimated. Estimation of R$_s$ may be made by any one or more of the following methods: using an empirical lookup table; and/or using a function such as described in the above mentioned Kirkeeide reference; and/or by a cumulative summation of Poiseuille resistances:

$$R_s = \frac{128\mu}{\pi} \int \frac{dl}{d^4}$$ Equation 5.17 where integration is over samples of the segment (dl), d is optionally an arterial diameter of each sample, and μ is 0.035 g·cm$^{-1}$·s$^{-1}$, optionally blood viscosity. The segment's downstream resistance is calculated for the segment R$_n$, [mmHg*s/mL] as follows:

$$R_n = R_t - R_s$$ Equation 5.18

A normal flow through the segment without stenosis Q$_n$, [mL/s], is calculated for example as follows:

$$Q_n = \frac{P_a}{R_n}$$ Equation 5.19 where Q$_n$ is an input flow to the segment, P$_a$ is pressure proximal to the segment, and R$_n$ is resistance to flow by vessels distal to the segment.

Another form of Fractional Flow Reserve (FFR$_{contrast-flow}$) is optionally derived as a ratio between measured flow rate through the stenosed segment and normal flow rate through the segment without stenosis:

$$FFR = \frac{Q_s}{Q_n}$$ Equation 5.20

In some embodiments, an index indicative of the potential effect of revascularization, such as an FFR index (for example, FFR$_{contrast-flow}$), is calculated using the data described below:

proximal arterial pressure P$_a$, [mmHg] is measured;
a total inlet flow through a vessel origin, such as the coronary origin Q$_{total}$, [mL/s], is derived from a concentration of contrast material (such as iodine), optionally based on the analysis of concentration-distance-time curves. In some embodiments, especially for large vessels such as the Left Anterior Descending (LAD) coronary artery, flow is optionally recorded using a transthoracic echo Doppler and/or other modalities such as MRI and SPECT;

a subject's specific anatomy, including one or more of the following:

a geometric description of arterial diameters along vessel tree segments, for example up to 3-4 generations as a function of segment length d(l) [cm];

a geometric description of arterial lengths along the vessel tree segments ($L_i$ [cm]), for example up to 1-2 generations downstream of the segment of interest, and an accumulative crown length ($L_{crown}$ [cm]) downstream to the segment of interest: $L_{crown} = \Sigma L_i$;

a geometric description of arterial volumes along the vessel tree segments $V_i$ [ml], for example up to 1-2 generations downstream of the segment of interest, and the accumulative crown volume ($V_{crown}$ [ml]) downstream to the segment of interest: $V_{crown} = \Sigma V_i$;

a myocardial mass (LV mass) distribution for the arterial segment of interest M [ml] (in some embodiments LV mass is optionally calculated using, for example, a transthoracic echo Doppler);

and a reference parameter K or function F which correlates anatomic parameters such as described above with normal flow through the segment (without stenosis) $Q_n$, [mL/s], for example:

$$Q_n = K \cdot M \text{ or } Q_n = F(M) \qquad \text{Equation 5.21}$$

Using the above data, the index indicative of the potential effect of revascularization, such as the FFR index, is optionally calculated by performing the following calculations for each vessel segment under consideration:

from the geometric parameter of the tree, such as length, volume, mass and/or diameter, a normal flow $Q_n$ in the segment is obtained;

from arterial pressure a resistance distal to the segment ($R_n$, [mmHg*s/mL]) is calculated, for example as follows: $R_n = P_d/Q_n$;

from geometry a local resistance of the stenosis in the segment $R_s$, [mmHg*s/mL] is estimated, for example using one of the following methods:

a lookup table;

an empirical function such as described in the above mentioned Kirkeeide reference; and/or a cumulative summation of Poiseuille resistances $R_s = (128\mu)/\pi \int (dl)/(d^4)$ where the integration is over samples of the segment (dl), d is an arterial diameter of each sample, and $\mu$ is 0.035 g·cm$^{-1}$·s$^{-1}$ is optionally blood viscosity;

the total resistance for the segment $R_t$ [mmHg*s/mL] is optionally calculated as: $R_t = R_n + R_s$ the flow through the stenosis segment $Q_s$ [mL/s] is optionally calculated as: $Q_s = P_d/R_t$; and the index, such as the fractional flow reserve (FFR), for the segment is optionally calculated as: $FFR = Q_s/Q_n$.

In some embodiments, the extent of the first model is such that it includes a stenosis, and extends distally as far as resolution of the imaging modality which produced the vessel model allows, and/or several bifurcations, for example 3 or 4 bifurcations distally to the stenosis. In some embodiments, the number of bifurcations is limited by the resolution to which vascular width can be determined from an image. For example, cutoff of the bifurcation order is set where the vascular width is no longer determinable to within a precision of 5%, 10%, 15%, 20%, or another larger, smaller, or intermediate precision. In some embodiments, sufficient precision is unavailable due, for example, to insufficient imaging resolution in the source images. Availability of a larger number of measurable bifurcations is a potential advantage for fuller reconstruction of the detailed vascular resistance in the crown vessels of a stenosis. It should be noted that in the current state of the art, CT scans generally provide a lower resolution than X-ray angiographic imaging, leading to a lowered availability of blood vessels from which vascular resistances can be determined.

CONCLUSION

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. An apparatus for synchronizing a three-dimensional model of a patient's coronary arteries with an orientation of a medical imaging device, the apparatus comprising:

a memory device storing a three-dimensional model of a patient's coronary arteries, the three-dimensional model including a centerline through each of the coronary arteries, each centerline having sample points, each sample point along the respective centerline being defined in a three-dimensional coordinate system and being associated with vascular geometric information; and a processor communicatively coupled to the memory device, the processor configured to:

receive an instruction to register the three-dimensional model to a medical imaging device, determine an orientation of the three-dimensional model that corresponds to a zero-degree starting position of the medical imaging device, receive potential rotational angulation positions of the medical imaging device, determine angular coordinates for the three-dimensional model that correspond to the potential rotational angulation positions of the medical imaging device, store to the memory device a correlation between the determined angular coordinates for the three-dimensional model and the potential rotational angulation positions of the medical imaging device, determine a current view angle orientation of the medical imaging device, use the correlation between the determined angular coordinates for the three-dimensional model and the potential rotational angulation positions of the medical imaging device to rotate the three-dimensional model using the current view angle orientation of the medical imaging device, and display the rotated three-dimensional model in a user interface in a viewpoint orientation that matches the current view angle orientation of the medical imaging device, wherein the user interface is configured to:

respond to user input to record a medical image and cause transmission of instructions to the medical imaging device, wherein the recorded medical image is displayed in conjunction with the three-dimensional model, and wherein based on a lock control being enabled, cause the medical imaging device to rotate in real-time synchronized with three-dimensional model, and based on the lock control not being enabled, allow the three-dimensional model to rotate without causing the medical imaging device to rotate in real-time.

2. The apparatus of claim 1, wherein the processor is further configured to determine the orientation of the three-dimensional model by identifying a two-dimensional face or a plane of the three-dimensional model that aligns with a view angle at the zero-degree starting position of an image intensifier of the medical imaging device, wherein the identified two-dimensional face of the plane of the three-dimensional model corresponds to a top-down view of the patient's coronary arteries when the patient is laying supine.

3. The apparatus of claim 1, wherein the vascular geometric information includes at least one of a vascular diameter, a vascular radius, a cross sectional area, a cross sectional profile, a vascular wall curvature, or vascular branching.

4. The apparatus of claim 1, wherein the medical imaging device includes a C-arm configured to record x-ray angiographic images.

5. The apparatus of claim 1, wherein the potential rotational angulation positions of the medical imaging device include RAO angulation positions, LAO angulation positions, cranial angulation positions, and caudal angulation positions.

6. The apparatus of claim 5, wherein the angular coordinates for the three-dimensional model include coordinates along a roll axis and a pitch axis.

7. The apparatus of claim 6, wherein the angular coordinates correspond to an amount the three-dimensional model is rotated along the roll axis and the pitch axis.

8. The apparatus of claim 5, wherein the potential rotational angulation positions of the medical imaging device are at least one of stored in the memory device, received from the medical imaging device, or received via user input via an interface.

9. The apparatus of claim 1, wherein the processor is further configured to:
receive from the medical imaging device a message that is indicative of at least one of (i) a relative position change from the zero-degree starting position of the medical imaging device provided in a rotational angulation position, or (ii) an absolute position of the medical imaging device provided in a rotational angulation position;
determine a new viewpoint orientation for the three-dimensional model based on the at least one of (i) or (ii) and the correlation between the determined angular coordinates for the three-dimensional model and the potential rotational angulation positions of the medical imaging device;
rotate the three-dimensional model to the new viewpoint orientation; and
display in the user interface the rotated three-dimensional model.

10. The apparatus of claim 9, wherein the processor is further configured to:
receive, via the user interface, an imaging message indicative that a medical image is to be acquired;
transmit an imaging instruction message to the medical imaging device; and
receive the medical image, the medical image acquired by the medical imaging device in the new viewpoint orientation.

11. The apparatus of claim 10, wherein the processor is further configured to:
identify coronary arteries in the medical image; determine centerlines through the identified coronary arteries;
determine sample points along the centerlines in the three-dimensional coordinate system;
determine vascular geometric information for the sample points along the centerline;
determine a correspondence between the coronary arteries in the medical image and the three-dimensional model using at least the centerlines of the medical image and the centerlines of the three-dimensional model; and
update the three-dimensional model with the determined vascular geometric information from the medical image.

12. The apparatus of claim 10, wherein the imaging instruction message includes at least one of an indication to record the medical image, a rotation instruction, a lateral movement instruction, or a zoom-magnification instruction.

13. The apparatus of claim 10, wherein the processor is configured to calculate and display, in the user interface, fractional flow reserve ("FFR") values for the three-dimensional model.

14. The apparatus of claim 1, wherein the memory device is located remotely from the processor.

15. A method for synchronizing a three-dimensional model of a patient's coronary arteries with an orientation of a medical imaging device, the method comprising:
receiving, in a processor from a memory device, a three-dimensional model of a patient's coronary arteries, the three-dimensional model including a centerline through each of the coronary arteries, each centerline including sample points, each sample point along the respective centerline being defined in a three-dimensional coordinate system and being associated with vascular geometric information;
determining, via the processor, an orientation of the three-dimensional model that corresponds to a zero-degree starting position of a medical imaging device;
receiving, in the processor, potential rotational angulation positions of the medical imaging device;
determining, via the processor, angular coordinates for the three-dimensional model that correspond to the potential rotational angulation positions of the medical imaging device;
storing, to the memory device via the processor, a correlation between the determined angular coordinates for the three-dimensional model and the potential rotational angulation positions of the medical imaging device;
determining, via the processor, a current viewpoint of the three-dimensional model displayed in a user interface; and
using, via the processor, the current viewpoint of the three-dimensional model and the correlation between the angular coordinates for the three-dimensional model and the potential rotational angulation positions of the medical imaging device to cause the medical image device to rotate to a corresponding view angle orientation based on a lock control being enabled.

16. The method of claim 15, wherein the medical imaging device includes a C-arm and the method is performed in a catheterization laboratory during at least one of a stent placement, a percutaneous coronary intervention, or an FFR determination.

17. The method of claim 15, further comprising:
receiving, in the processor, for the medical imaging device, at least two medical images recorded at different view angles with respect to the patient, the at least two medical images including depictions of the patient's coronary arteries;
identifying, via the processor, the coronary arteries in the at least two medical images;
determining, via the processor, centerlines through the identified coronary arteries;
determining, via the processor, sample points along the centerlines in the three-dimensional coordinate system;
determining, via the processor, vascular geometric information for the sample points along the centerlines;
creating the three-dimensional model using the centerlines, the sample points along the centerlines in the three-dimensional coordinate system, and the vascular geometric information; and
storing the three-dimensional model to the memory device.

18. The method of claim 15, wherein the processor causes the medical image device to rotate by transmitting at least one instruction message to the medical image device, the at least one instruction message including at least one of (i) a relative position change from the zero-degree starting position positon of the medical imaging device to the corresponding view angle orientation provided in a rotational angulation position, or (ii) an absolute position of the medical imaging device for the corresponding view angle orientation provided in a rotational angulation position.

19. The method of claim 15, wherein the potential rotational angulation positions of the medical imaging device include RAO angulation positions, LAO angulation positions, cranial angulation positions, and caudal angulation positions, and
wherein the angular coordinates for the three-dimensional model include coordinates along a roll axis and a pitch axis.

20. The method of claim 15, wherein based on the lock control not being enabled, movement of the medical imaging device is disregarded thereby enabling the medical imaging device to be rotated without affecting display of the three-dimensional model.

21. The method of claim 15, wherein the processor is configured to display an alert indicative that movement of the three-dimensional model is outside a movement capability of the medical imaging device.

* * * * *